(12) United States Patent  (10) Patent No.: US 8,744,570 B2
Lee et al.  (45) Date of Patent: Jun. 3, 2014

(54) OPTICAL STIMULATION OF THE BRAINSTEM AND/OR MIDBRAIN, INCLUDING AUDITORY AREAS

(75) Inventors: Daniel J. Lee, Cambridge, MA (US); Jonathon D. Wells, Seattle, WA (US)

(73) Assignee: Lockheed Martin Corporation, Bethesda, MD (US)

( * ) Notice: Subject to any disclaimer, the term of this patent is extended or adjusted under 35 U.S.C. 154(b) by 692 days.

(21) Appl. No.: 12/693,427

(22) Filed: Jan. 25, 2010

(65) Prior Publication Data

US 2010/0292758 A1 Nov. 18, 2010

Related U.S. Application Data

(60) Provisional application No. 61/147,073, filed on Jan. 23, 2009.

(51) Int. Cl.
 *A61N 1/36* (2006.01)
 *A61N 1/08* (2006.01)

(52) U.S. Cl.
 USPC .................. 607/3; 607/115; 607/54; 607/55

(58) Field of Classification Search
 USPC .............................. 607/1–3, 53–57, 115, 116
 See application file for complete search history.

(56) References Cited

U.S. PATENT DOCUMENTS

| 4,064,872 A | 12/1977 | Caplan |
| 4,215,694 A | 8/1980 | Isakov et al. |
| 4,232,678 A | 11/1980 | Skovajsa |
| 4,296,995 A | 10/1981 | Bickel |
| 4,558,703 A | 12/1985 | Mark |

(Continued)

FOREIGN PATENT DOCUMENTS

| WO | WO 0025112 | 5/2000 |
| WO | PCTUS0951080 | 11/2009 |
| WO | PCTUS0959591 | 11/2009 |

OTHER PUBLICATIONS

Allegre, et al., "Stimulation in the rat of a nerve fiber bundle by a short UV pulse from an excimer laser", "NeuroScience Letters", 1994, pp. 261-264, vol. 180.

(Continued)

*Primary Examiner* — Brian T Gedeon
(74) *Attorney, Agent, or Firm* — Charles A. Lemaire; Jonathan M. Rixen; Lemaire Patent Law Firm, P.L.L.C.

(57) ABSTRACT

Apparatus and method for optical- or optical-and-electrical stimulation of midbrain and/or brainstem tissue (e.g., auditory nerve pathways). Peripheral neural stimulation using infrared lasers has been demonstrated in several systems; however, optical stimulation of the central nervous system (CNS) has not been previously described. In some embodiments of the present invention, radiant energy exposure of the cochlear nucleus using a mid-wavelength infrared laser generates optically-evoked auditory brainstem responses (oABRs). In an experiment, the cochlear nuclei of adult male Sprague-Dawley rats were exposed using a suboccipital craniotomy approach. In one embodiment, different regions of left cochlear nucleus were acutely stimulated with a 200- or 400-micron-diameter optical fiber placed on the surface of the brainstem, using 50- to 750-microsecond pulses of 1849-nm to 1865-nm-wavelength radiation at a rate of 10 to 40 Hz and power levels ranging from 10% to 80% of 5 watts. oABRs were recorded during the period of optical stimulation.

22 Claims, 12 Drawing Sheets
(10 of 12 Drawing Sheet(s) Filed in Color)

(56) References Cited

U.S. PATENT DOCUMENTS

| | | |
|---|---|---|
| 4,566,935 A | 1/1986 | Hornbeck |
| 4,596,992 A | 6/1986 | Hornbeck |
| 4,671,285 A | 6/1987 | Walker |
| 4,681,791 A | 7/1987 | Shibahashi et al. |
| 4,724,835 A | 2/1988 | Liss et al. |
| 4,768,516 A | 9/1988 | Stoddart et al. |
| 4,813,418 A | 3/1989 | Harris |
| 4,840,485 A | 6/1989 | Gratton |
| 4,928,695 A | 5/1990 | Goldman et al. |
| 4,930,504 A | 6/1990 | Diamantopoulos et al. |
| 4,972,331 A | 11/1990 | Chance |
| 4,989,605 A | 2/1991 | Rossen |
| 5,062,428 A | 11/1991 | Chance |
| 5,088,493 A | 2/1992 | Giannini et al. |
| 5,122,974 A | 6/1992 | Chance |
| 5,139,025 A | 8/1992 | Lewis et al. |
| 5,150,704 A | 9/1992 | Tatebayashi et al. |
| 5,151,909 A | 9/1992 | Davenport et al. |
| 5,152,278 A | 10/1992 | Clayman |
| 5,187,672 A | 2/1993 | Chance et al. |
| 5,192,278 A | 3/1993 | Hayes et al. |
| 5,212,386 A | 5/1993 | Gratton et al. |
| 5,213,093 A | 5/1993 | Swindle |
| 5,213,105 A | 5/1993 | Gratton et al. |
| 5,257,202 A | 10/1993 | Feddersen et al. |
| 5,259,382 A | 11/1993 | Kronberg |
| 5,261,822 A | 11/1993 | Hall et al. |
| 5,323,010 A | 6/1994 | Gratton et al. |
| 5,327,902 A | 7/1994 | Lemmen |
| 5,353,799 A | 10/1994 | Chance |
| 5,386,827 A | 2/1995 | Chance et al. |
| 5,402,778 A | 4/1995 | Chance |
| 5,419,312 A | 5/1995 | Arenberg et al. |
| 5,430,175 A | 7/1995 | Hess et al. |
| 5,445,146 A | 8/1995 | Bellinger |
| 5,464,960 A | 11/1995 | Hall et al. |
| 5,480,482 A | 1/1996 | Novinson |
| 5,484,432 A | 1/1996 | Sand |
| 5,548,604 A | 8/1996 | Toepel |
| 5,553,614 A | 9/1996 | Chance |
| 5,564,417 A | 10/1996 | Chance |
| 5,608,519 A | 3/1997 | Gourley et al. |
| 5,664,574 A | 9/1997 | Chance |
| 5,704,899 A | 1/1998 | Milo |
| 5,754,578 A | 5/1998 | Jayaraman |
| 5,755,752 A | 5/1998 | Segal |
| 5,792,051 A | 8/1998 | Chance |
| 5,796,889 A | 8/1998 | Xu et al. |
| 5,799,030 A | 8/1998 | Brenner |
| 5,851,223 A | 12/1998 | Liss et al. |
| 5,899,865 A | 5/1999 | Chance |
| 5,913,884 A | 6/1999 | Trauner et al. |
| 6,033,431 A | 3/2000 | Segal |
| 6,048,359 A | 4/2000 | Biel |
| 6,066,127 A | 5/2000 | Abe |
| 6,074,411 A | 6/2000 | Lai et al. |
| 6,104,957 A | 8/2000 | Alo et al. |
| 6,110,195 A | 8/2000 | Xie et al. |
| 6,152,882 A | 11/2000 | Prutchi |
| 6,171,239 B1 | 1/2001 | Humphrey |
| 6,184,542 B1 | 2/2001 | Alphonse |
| 6,224,969 B1 | 5/2001 | Steenbergen et al. |
| 6,246,892 B1 | 6/2001 | Chance |
| 6,257,759 B1 | 7/2001 | Witonsky et al. |
| 6,258,082 B1 | 7/2001 | Lin |
| 6,263,221 B1 | 7/2001 | Chance et al. |
| 6,267,779 B1 | 7/2001 | Gerdes |
| 6,272,367 B1 | 8/2001 | Chance |
| 6,284,078 B1 | 9/2001 | Witonsky et al. |
| 6,294,109 B1 | 9/2001 | Ratna et al. |
| 6,301,279 B1 | 10/2001 | Garbuzov et al. |
| 6,310,083 B1 | 10/2001 | Kao et al. |
| 6,312,451 B1 | 11/2001 | Streeter |
| 6,314,324 B1 | 11/2001 | Lattner et al. |
| 6,324,429 B1 | 11/2001 | Shire et al. |
| 6,330,388 B1 | 12/2001 | Bendett et al. |
| 6,339,606 B1 | 1/2002 | Alphonse |
| 6,353,226 B1 | 3/2002 | Khalil et al. |
| 6,358,272 B1 | 3/2002 | Wilden |
| 6,363,188 B1 | 3/2002 | Alphonse |
| 6,417,524 B1 | 7/2002 | Alphonse |
| 6,421,474 B2 | 7/2002 | Jewell et al. |
| 6,444,313 B1 | 9/2002 | Ono et al. |
| 6,456,866 B1 | 9/2002 | Tyler et al. |
| 6,459,715 B1 | 10/2002 | Khalfin et al. |
| 6,475,800 B1 | 11/2002 | Hazen et al. |
| 6,488,704 B1 | 12/2002 | Connelly et al. |
| 6,493,476 B2 | 12/2002 | Bendett |
| 6,505,075 B1 | 1/2003 | Weiner |
| 6,542,530 B1 | 4/2003 | Shieh et al. |
| 6,542,772 B1 | 4/2003 | Chance |
| 6,546,291 B2 | 4/2003 | Merfeld et al. |
| 6,556,611 B1 | 4/2003 | Khalfin et al. |
| 6,564,076 B1 | 5/2003 | Chance |
| 6,585,411 B2 | 7/2003 | Hammarth et al. |
| 6,592,611 B1 | 7/2003 | Zawada |
| 6,630,673 B2 | 10/2003 | Khalil et al. |
| 6,636,678 B1 | 10/2003 | Bendett et al. |
| 6,639,930 B2 | 10/2003 | Griffel et al. |
| 6,669,379 B2 | 12/2003 | Janosik et al. |
| 6,669,765 B2 | 12/2003 | Senga et al. |
| 6,688,783 B2 | 2/2004 | Janosik et al. |
| 6,690,873 B2 | 2/2004 | Bendett et al. |
| 6,735,474 B1 | 5/2004 | Loeb et al. |
| 6,735,475 B1 | 5/2004 | Whitehurst et al. |
| 6,744,548 B2 | 6/2004 | Abeles |
| 6,746,473 B2 | 6/2004 | Shanks et al. |
| 6,748,275 B2 | 6/2004 | Lattner et al. |
| 6,823,109 B2 | 11/2004 | Sasaki et al. |
| RE38,670 E | 12/2004 | Asah et al. |
| 6,836,685 B1 | 12/2004 | Fitz |
| 6,871,084 B1 | 3/2005 | Kingsley et al. |
| 6,902,528 B1 | 6/2005 | Garibaldi et al. |
| 6,909,826 B2 | 6/2005 | Cai et al. |
| 6,920,358 B2 * | 7/2005 | Greenberg et al. ............. 607/54 |
| 6,921,413 B2 | 7/2005 | Mahadevan-Jansen et al. |
| 6,956,650 B2 | 10/2005 | Boas et al. |
| 6,980,579 B2 | 12/2005 | Jewell |
| 6,989,023 B2 | 1/2006 | Black |
| 7,003,353 B1 | 2/2006 | Parkhouse |
| 7,004,645 B2 | 2/2006 | Lemoff et al. |
| 7,006,749 B2 | 2/2006 | Illich et al. |
| 7,010,341 B2 | 3/2006 | Chance |
| 7,031,363 B2 | 4/2006 | Biard et al. |
| 7,040,805 B1 | 5/2006 | Ou et al. |
| 7,068,878 B2 | 6/2006 | Crossman-Bosworth et al. |
| 7,069,083 B2 | 6/2006 | Finch et al. |
| 7,079,900 B2 | 7/2006 | Greenburg et al. |
| 7,085,300 B2 | 8/2006 | Werner et al. |
| 7,095,770 B2 | 8/2006 | Johnson |
| 7,116,886 B2 | 10/2006 | Colgan et al. |
| 7,139,603 B2 | 11/2006 | Chance |
| 7,156,866 B1 | 1/2007 | Riggs et al. |
| 7,177,081 B2 | 2/2007 | Tomita et al. |
| 7,194,063 B2 | 3/2007 | Dilmanian et al. |
| 7,225,028 B2 * | 5/2007 | Della Santina et al. ......... 607/57 |
| 7,231,256 B2 | 6/2007 | Wahlstrand et al. |
| 7,244,253 B2 | 7/2007 | Neev |
| 7,302,296 B1 | 11/2007 | Hoffer |
| 7,311,722 B2 | 12/2007 | Larsen |
| 7,324,852 B2 | 1/2008 | Barolat et al. |
| 7,329,251 B2 | 2/2008 | Yamada et al. |
| 7,337,004 B2 | 2/2008 | Classen et al. |
| 7,391,561 B2 | 6/2008 | Di Teodoro et al. |
| 7,402,167 B2 | 7/2008 | Nemenov |
| 7,433,598 B2 | 10/2008 | Schemmann et al. |
| 7,647,112 B2 | 1/2010 | Tracey et al. |
| 7,654,750 B2 | 2/2010 | Brenner et al. |
| 7,736,382 B2 * | 6/2010 | Webb et al. ..................... 607/89 |
| 7,776,631 B2 | 8/2010 | Miles |
| 7,787,170 B2 | 8/2010 | Patel et al. |
| 7,792,588 B2 | 9/2010 | Harding |
| 7,797,029 B2 | 9/2010 | Gibson et al. |
| 7,833,257 B2 * | 11/2010 | Walsh et al. ..................... 607/88 |

(56) References Cited

U.S. PATENT DOCUMENTS

| | | | |
|---|---|---|---|
| 7,873,085 B2 | 1/2011 | Babushkin et al. | |
| 7,883,535 B2* | 2/2011 | Cantin et al. | 607/89 |
| 7,883,536 B1 | 2/2011 | Bendett et al. | |
| 7,894,905 B2* | 2/2011 | Pless et al. | 607/46 |
| 7,909,867 B2 | 3/2011 | Myung et al. | |
| 7,914,842 B1 | 3/2011 | Greenberg et al. | |
| 7,951,181 B2 | 5/2011 | Mahadevan-Jansen et al. | |
| 7,988,688 B2* | 8/2011 | Webb et al. | 606/13 |
| 8,012,189 B1* | 9/2011 | Webb et al. | 607/89 |
| 2002/0002391 A1 | 1/2002 | Gerdes | |
| 2002/0123781 A1 | 9/2002 | Shanks et al. | |
| 2002/0147400 A1 | 10/2002 | Chance | |
| 2003/0083724 A1 | 5/2003 | Jog et al. | |
| 2003/0236458 A1 | 12/2003 | Hochman | |
| 2004/0073101 A1 | 4/2004 | Chance | |
| 2005/0143789 A1 | 6/2005 | Whitehurst et al. | |
| 2006/0167564 A1 | 7/2006 | Flaherty et al. | |
| 2006/0276861 A1 | 12/2006 | Lin | |
| 2007/0191906 A1 | 8/2007 | Iyer et al. | |
| 2007/0260297 A1 | 11/2007 | Chariff | |
| 2008/0299201 A1* | 12/2008 | Kozloski et al. | 424/484 |
| 2009/0054954 A1* | 2/2009 | Foley et al. | 607/88 |
| 2009/0076115 A1 | 3/2009 | Wharton et al. | |
| 2009/0163982 A1 | 6/2009 | deCharms | |
| 2009/0210039 A1 | 8/2009 | Boyden et al. | |
| 2010/0049180 A1 | 2/2010 | Wells et al. | |
| 2010/0114190 A1 | 5/2010 | Bendett et al. | |
| 2010/0145418 A1 | 6/2010 | Zhang et al. | |
| 2010/0162109 A1 | 6/2010 | Chatterjee et al. | |
| 2010/0174329 A1* | 7/2010 | Dadd et al. | 607/3 |
| 2010/0174330 A1* | 7/2010 | Dadd et al. | 607/3 |
| 2010/0174344 A1* | 7/2010 | Dadd et al. | 607/57 |
| 2010/0184818 A1 | 7/2010 | Wharton et al. | |
| 2010/0197995 A1* | 8/2010 | Wenzel et al. | 600/25 |
| 2010/0198317 A1* | 8/2010 | Lenarz et al. | 607/89 |
| 2010/0262212 A1* | 10/2010 | Shoham et al. | 607/88 |
| 2011/0172725 A1 | 7/2011 | Wells et al. | |

OTHER PUBLICATIONS

Arridge, et al., "The theoretical basis for the determination of optical pathlengths in tissue: temporal and frequency analysis", "Phys. Med. Biol.", 1992, pp. 1531-1560, vol. 37.

Chance, et al., "Comparison of time-resolved and -unresolved measurements of deoxyhemoglobin in brain", "Proc. Natl. Acad. Sci. USA", Jul. 1988, pp. 4971-4975, vol. 85.

Desmurget, et al., "Movement Intention after Parietal Cortex Stimulation in Humans", "Science", May 8, 2009, pp. 811-813, vol. 324.

Fork, Richard L., "Laser Stimulation of Nerve Cells in Aplysia", "Science, New Series", Mar. 5, 1971, pp. 907-908, vol. 171, No. 3974.

Haggard, "The Sources of Human Volition", "Science", May 8, 2009, pp. 731-733, vol. 324.

Izzo, et al., "Laser Stimulation of the Auditory Nerve", "Lasers in Surgery and Medicine", 2006, Publisher: Wiley-Liss, Inc.

Izzo, et al., "Selectivity of neural stimulation in the auditory system: an comparison of optic and electric stimuli", "Journal of Biomedical Optics", Mar./Apr. 2007, p. 021008 , vol. 12, No. 2.

Izzo, Agnella D., et al., "Optical Parameter Variability in Laser Nerve Stimulation: A Study of Pulse Duration, Repetition Rate, and Wavelength.", "IEEE Transactions on Biomedical Engineering", Jun. 2007, p. 1108-1114, vol. 54, No. 6(1).

Maiorov, M., et al., "218 W quasi-CW operation of 1.83 um two-dimensional laser diode array", "Electronics Letters", Apr. 15, 1999, pp. 636-638, vol. 35, No. 8.

Nakagawa, Atsuhiro, et al., "Pulsed holmium:yttrium-aluminum-garnet laser-induced liquid jet as a novel dissection device in neuroendoscopic surgery", "J. Neurosurg. ", Jul. 2004 , pp. 145-150, vol. 10.

Passos, D., et al., "Tissue phantom for optical diagnostics based on a suspension of microspheres with a fractal size distribution", "Journal of Biomedical Optics. ", Nov.-Dec. 2005 , p. 064036, vol. 10, No. 6.

Princeton Lightwave (Company), "High Power Multimode Laser Arrays", "www.princetonlightwave.com/content/pli_high_power_multimode_laser_arrays.pdf", 2005.

Princeton Lightwave (Company), "High Power Water Cooled Laser Stack", "www.princetonlightwave.com", 2005.

Princeton Lightwave (Company), "High Power Single Element Laser", "www.princetonlightwave.com/content/HP%20Single%20Element%20Laser%20version%202.pdf", 2005.

Rolfe, "In Vivo Near-Infrared Spectroscopy", "Annu. Rev. Biomed. Eng.", 2000, pp. 715-754 , vol. 2.

Schwartz, et al., "Auditory Brainstem Implants", "Neurotherapeutics: The Journal of the American Society for Experimental NeuroTherapeutics", Jan. 2008, pp. 128-136, vol. 5.

Tarler, et al., "Comparison of joint torque evoked with monopolar and tripolar-cuff electrodes", "IEEE Trans Neural Syst Rehabil Eng", 2003, pp. 227-235, vol. 11, No. 3.

Teudt, et al., "Optical Stimulation of the Facial Nerve: A New Monitoring Technique?", "The Laryngoscope", 2007, pp. 1641-1647, vol. 117, No. 9.

Wells, Jonathon, et al., "Application of Infrared Light for in vivo Neural Stimulation.", "Journal of Biomedical Optics ", Nov. 2005, pp. 064003-1 to 064003-12, vol. 10, No. 6.

Augustine, George J., "Combining patch-clamp and optical methods in brain slices", "Journal of Neuroscience Methods", 1994, pp. 163-169, vol. 54.

Banghart, Matthew, et al., "Light-activated ion channels for remote control of neuronal firing", "Nature Neuroscience", Nov. 21, 2004, pp. 1381-1386, vol. 7, No. 12.

Bernstein, Jacob G., et al., "Prosthetic systems for therapeutic optical activation and silencing of genetically-targeted neurons", "Proc Soc Photo Opt Instrum Eng.", May 5, 2008, vol. 6854: 68540H.

Boyden, Edward S., et al., "Millisecond-timescale, genetically targeted optical control of neural activity", "Nature Neuroscience ", Sep. 2005, pp. 1263-1268, vol. 8, No. 9.

Bureau, Ingrid, et al., "Precise Development of Functional and Anatomical Columns in the Neocortex", "Neuron", Jun. 10, 2004, pp. 789-801, vol. 42.

Chambers, James J., et al., "Light-Induced Depolarization of Neurons Using a Modified Shaker K+ Channel and a Molecular Photoswitch", "Journal of Neurophysiology", Jul 26, 2006, pp. 2792-2796, vol. 96.

Deal, Walter J., et al., "Photoregulation of Biol. Activity by Photochromic Reagents, 3. Photoreg. of Bioelectricity by Acetylcholine Receptor INH", "Proc. Natl. Acad. Sci.", 1969, pp.1230-1234, vol. 64, No. 4.

Dodt, H.-U., et al., "Circuitry of rat barrel cortex investigated by infrared-guided laser stimulation", "NeuroReport", Mar. 24, 2003, pp. 623-627, vol. 14, No. 4.

Dodt, H.-U., et al., "Precisely Localized LTD in the Neocortex Revealed by Infrared-Guided Laser Stimulation.", "Science", Oct 1, 1999, pp. 110-113, vol. 286.

Eder, Matthias, et al. , "Neocortical Long-Term Potentiation and Long-Term Depression: Site of Expression Investigated by IR-Guided Laser Stim.", "Journal of Neuroscience", Sep. 1, 2002, pp. 7558-7568, vol. 22, No. 17.

Han, Xue, et al., "Multiple-Color Optical Activation, Silencing, and Desynchronization of Neural Activity, with Single-Spike Temporal Resol", "PLoS One 2(3): e299. doi:10.1371/journal.pone.0000299", Mar. 2007, p. e299, No. 3, Publisher: www.plosone.org.

Huang, Ying-Ying, et al., "Biphasic Dose Response in Low Level Light Therapy", "Dose-Response", 2009, pp. 358-383, vol. 7.

Naples, et al., "A spiral nerve cuff electrode for peripheral nerve stimulation", "IEEE Trans Biomed Eng", Nov., 1988, pp. 905-916, vol. 35, No. 11.

Schiefer, et al., "A Model of Selective Activation of the Femoral Nerve with a Flat Interface Nerve Electrode for a Lower Extremity Neuropr", "IEEE Trans Neural Syst Rehabil Eng", Apr. 2008, pp. 195-204, vol. 16, No. 2.

Vogel, Alfred, et al., "Mechanisms of pulsed laser ablation of biological tissues.", "Chemical Reviews", 2003, pp. 577-644, vol. 103, No. 2.

(56) References Cited

OTHER PUBLICATIONS

Wells, Jonathon, et al., "Optical stimulation of neural tissue in vivo", "Optics Letters", Mar. 1, 2005, pp. 504-506, vol. 30, No. 5.

Wells, Jonathon D., et al., "Optically Mediated Nerve Stimulation: Identification of Injury Thresholds.", "Lasers in Surgery and Medicine", Jul. 23, 2007, pp. 513-526, vol. 39.

Wells, Jonathon, et al., "Pulsed laser versus electrical energy for peripheral nerve stimulation", "Journal of Neuroscience Methods", 2007, pp. 326-337, vol. 163.

Yoo, et al., "Selective recording of the canine hypoglossal nerve using a multicontact flat interface nerve electrode", "IEEE Trans Biomed Eng", Aug. 2005, pp. 1461-1469, vol. 52, No. 8.

Zemelman, Boris V., et al., "Photochemical gating of heterologous ion channels: Remote control over genetically designated populations of neurons", "Proceedings of the National Academy of Sciences", Feb. 4, 2003, pp. 1352-1357, vol. 100, No. 3.

Zhang, Feng, et al., "Channelrhodopsin-2 and optical control of excitable cells", "Nature Methods", Sep. 21, 2006, pp. 785-792, vol. 3, No. 10.

\* cited by examiner

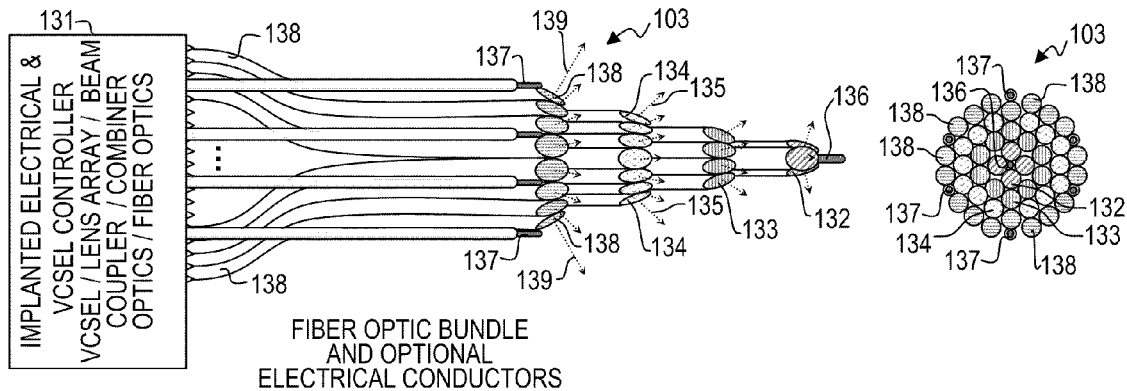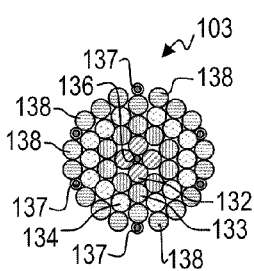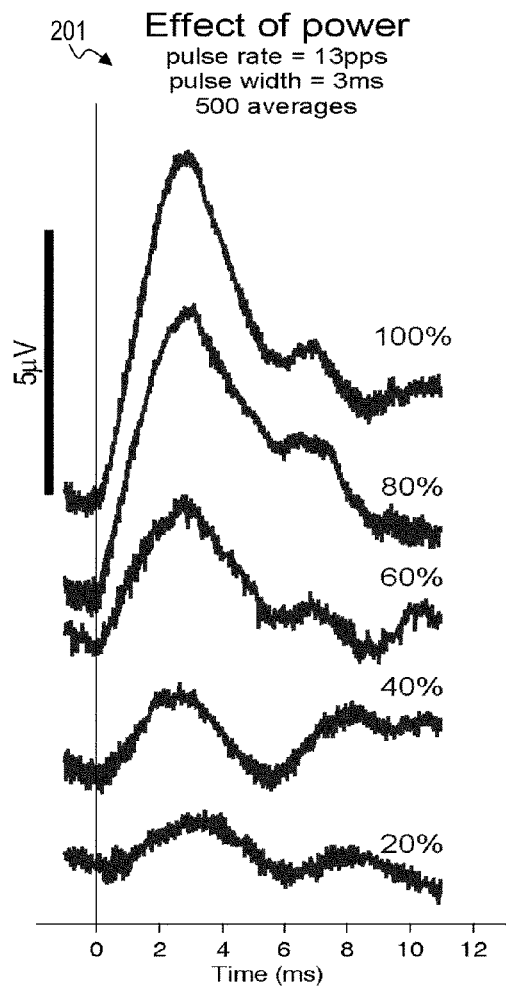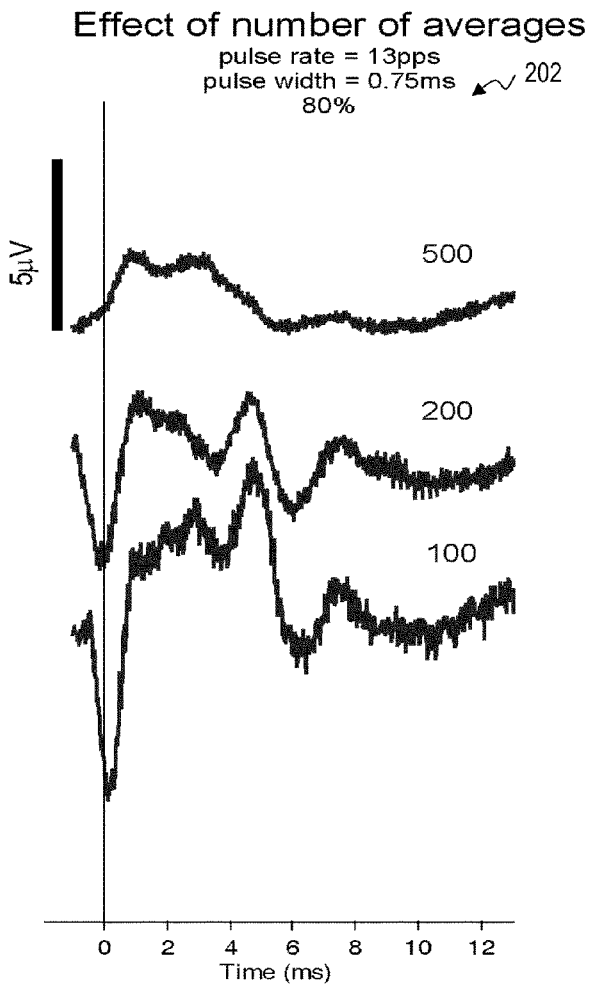

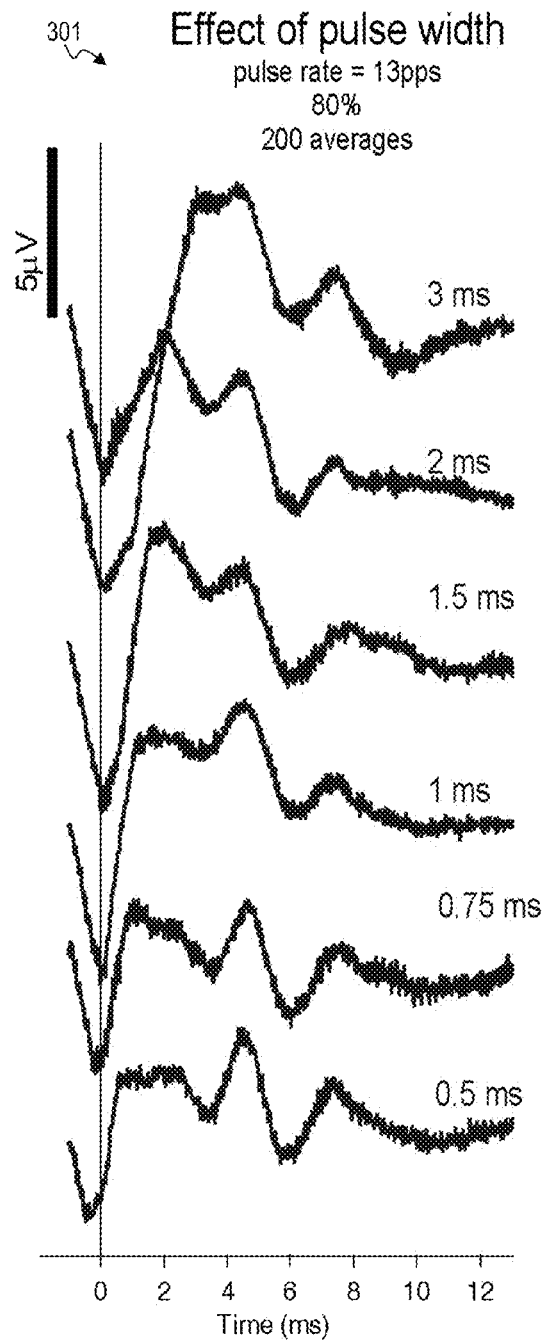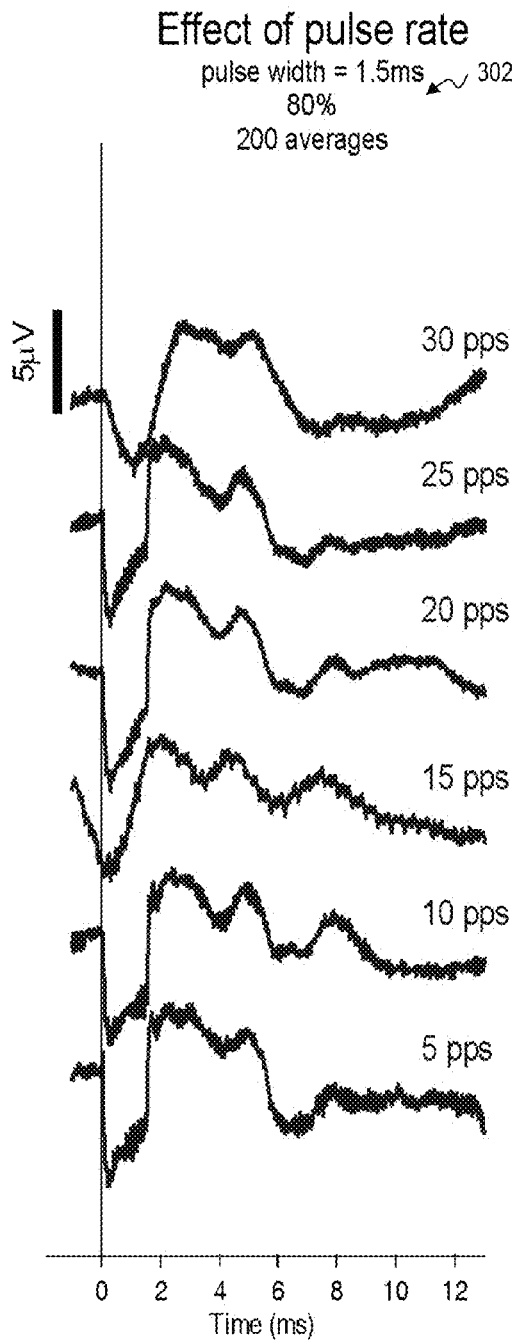
FIG. 3A — Effect of pulse width (pulse rate = 13pps, 80%, 200 averages)
FIG. 3B — Effect of pulse rate (pulse width = 1.5ms, 80%, 200 averages)

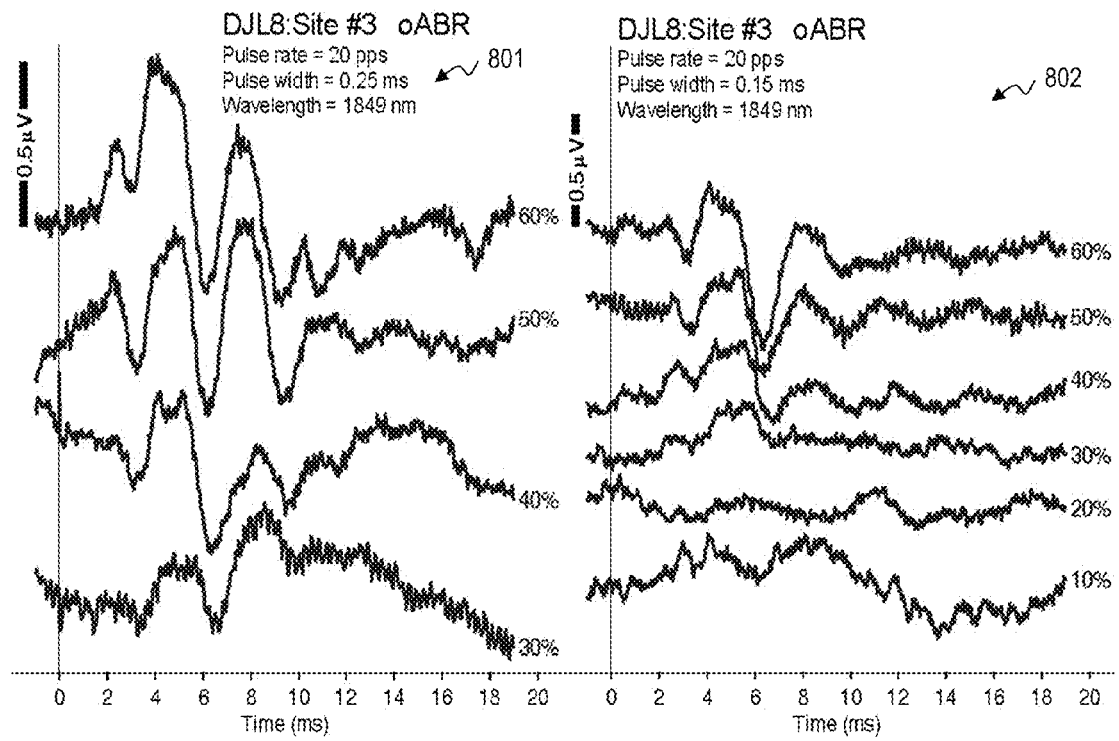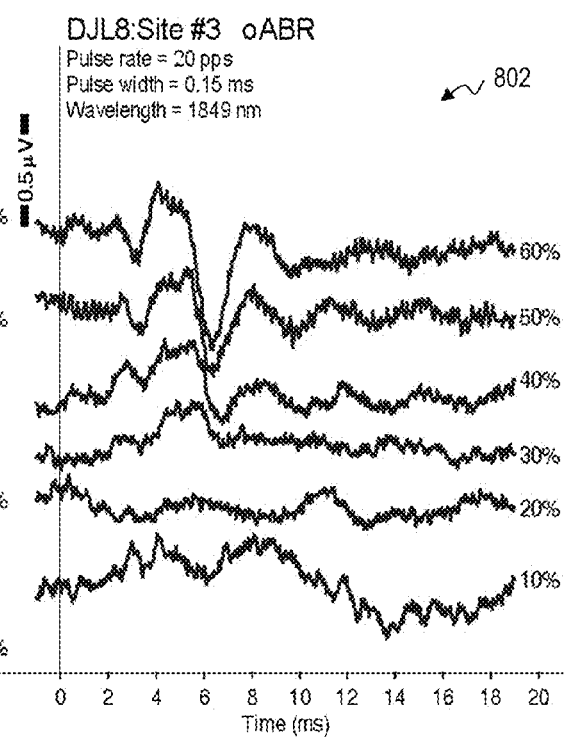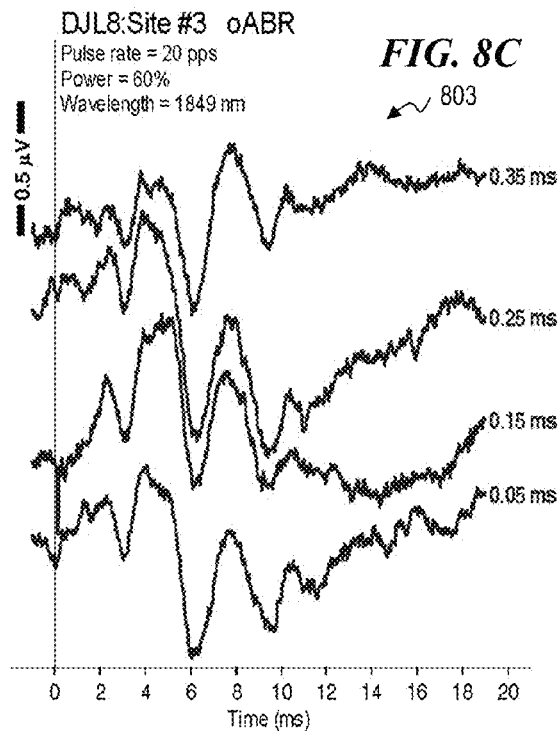

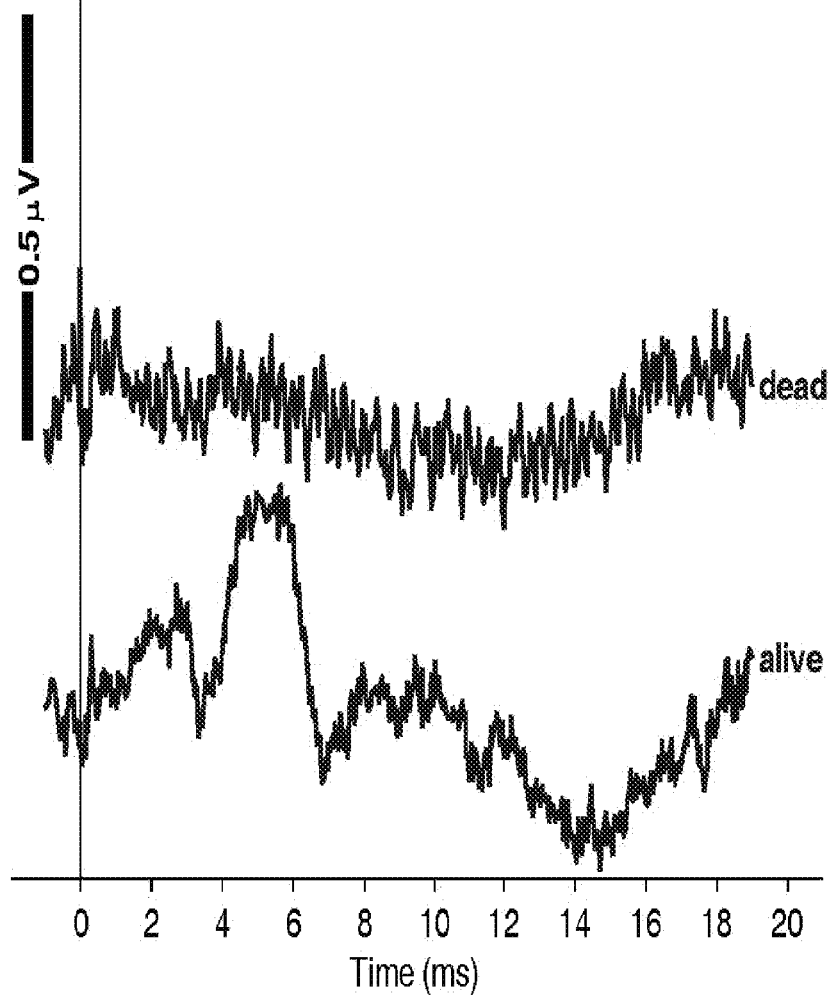

OPTICAL STIMULATION OF THE BRAINSTEM AND/OR MIDBRAIN, INCLUDING AUDITORY AREAS

RELATED APPLICATIONS

This application claims benefit under 35 U.S.C. §119(e) of U.S. Provisional Patent Application 61/147,073 filed on Jan. 23, 2009, titled "Optical Stimulation using Infrared Lasers (or in Combination with Electrical Stimulation) of the Auditory Brainstem and/or Midbrain," which is incorporated herein by reference in its entirety.

The present invention is related to prior

U.S. Provisional Patent Application No. 60/872,930 filed Dec. 4, 2006, titled "Apparatus and Method for Characterizing Optical Sources used with Human and Animal Tissues";

U.S. Provisional Patent Application No. 60/884,619 filed Jan. 11, 2007, titled "Vestibular Implant using Infrared Nerve Stimulation";

U.S. Provisional Patent Application No. 60/885,879 filed Jan. 19, 2007, titled "Hybrid Optical-Electrical Probes";

U.S. Provisional Patent Application No. 60/964,634 filed Aug. 13, 2007, titled "VCSEL Array Stimulator Apparatus and Method for Light Stimulation of Bodily Tissues";

U.S. Provisional Patent Application No. 61/015,665 filed Dec. 20, 2007, titled "Laser Stimulation of the Auditory System at 1.94 μm and Microsecond Pulse Durations";

U.S. Provisional Patent Application No. 61/102,811 filed Oct. 3, 2008, titled "Nerve Stimulator and Method using Simultaneous Electrical and Optical Signals";

U.S. patent application Ser. No. 11/257,793 filed Oct. 24, 2005, titled "Apparatus and Method for Optical Stimulation of Nerves and Other Animal Tissue"(which issued as U.S. Pat. No. 7,736,382 on Jun. 15, 2010);

U.S. patent application Ser. No. 11/536,639 filed Sep. 28, 2006, titled "Miniature Apparatus and Method for Optical Stimulation of Nerves and Other Animal Tissue"(which issued as U.S. Pat. No. 7,988,688 on Aug. 2, 2011);

U.S. patent application Ser. No. 11/948,912 filed Nov. 30, 2007, titled "Apparatus and Method for Characterizing Optical Sources used with Human and Animal Tissues";

U.S. patent application Ser. No. 11/536,642 filed Sep. 28, 2006, titled "Apparatus and Method for Stimulation of Nerves and Automated Control of Surgical Instruments";

U.S. patent application Ser. No. 11/971,874 filed Jan. 9, 2008, titled "Method and Vestibular Implant using Optical Stimulation of Nerves"(which issued as U.S. Pat. No. 8,012,189 on Sep. 6, 2011);

U.S. patent application Ser. No. 12/018,185 filed Jan. 22, 2008, titled "Hybrid Optical-Electrical Probes"(which issued as U.S. Pat. No. 7,883,536 on Feb. 8, 2011);

U.S. patent application Ser. No. 12/191,301 filed Aug. 13, 2008, titled "VCSEL Array Stimulator Apparatus and Method for Light Stimulation of Bodily Tissues"; and U.S. patent application Ser. No. 12/573,848 filed Oct. 5, 2009, titled "Nerve Stimulator and Method using Simultaneous Electrical and Optical Signals"(which issued as U.S. Pat. No. 8,160,696 on Apr. 17, 2012); each of which is incorporated herein by reference in its entirety.

FIELD OF THE INVENTION

The present invention relates to laser stimulation of animal tissues and more particularly to lasers and methods for making and using devices that generate optical signals, and optionally also electrical signals in combination with the optical signals, to stimulate and/or simulate an auditory signal in nerve and/or brain tissue of a living animal (e.g., a human) to treat deafness and provide sensations related to hearing, and/or to stimulate and/or simulate other "sensory" signals in nerve and/or brain tissue of a living animal (e.g., a human) to treat other sensory deficiencies (e.g., balance, visual or olfactory) and provide sensations related to those sensory deficiencies.

BACKGROUND OF THE INVENTION

As a convention used herein, a nerve will be defined as a collection of individual nerve fibers (i.e., axons) of individual nerve cells (neurons) that together form a set of nerve pathways (an integrated set of pathways for signal propagation within the nervous system). Subsets of the individual nerve fibers are each bundled into one of a plurality of fascicles that together form the nerve. Action potentials can occur in the axon portion of individual nerve cells. A series of individual nerve fibers that together form an integrated signal pathway starting at a sensory-receptor nerve ending and extending to the brain will be referred to as a sensory-nerve pathway, a series of individual nerve fibers that together form an integrated signal pathway starting at the brain and extending to a muscle cell will be referred to as a motor-nerve pathway. A sensory-nerve pathway that carries auditory signals will be referred to as an auditory-nerve pathway, and a sensory-nerve pathway that carries signals from the sense-of-balance organs (e.g., the vestibular organs of the inner ear, or perhaps the eyes) will be referred to as a sense-of-balance nerve pathway.

Within each fascicle of a nerve, there will typically be a plurality of sensory-nerve pathways and a plurality of motor-nerve pathways, wherein the number of sensory-nerve pathways will typically be about fifteen times as many as the number of motor-nerve pathways. As well, a series of individual nerve fibers may together form an integrated pathway starting at one of various internal organs and ending in the brain, with then other series of individual nerve fibers together forming an integrated pathway starting at the brain and extending to some internal end organ (such as the digestive tract, the heart, or blood vessels) as part of the autonomic nervous system; and a series of individual nerve fibers may together form an integrated pathway within the brain referred to as a tract. As used herein, a nerve bundle or fascicle refers to a collection of nerve fibers that subserve a like function (e.g., a fascicle may support a plurality of different motor-nerve pathways and thus motor-control signals needed for the muscles for a hand grasp, for example; similarly the same and/or a nearby fascicle may support a plurality of corresponding sensory-nerve pathways and thus sensory signals that provide the brain with feedback for the hand grasp).

Applying an electrical signal across or into a neuron (nerve cell), or a nerve bundle or nerve, is one way to stimulate a nerve action potential (NAP), either in a single neuron (nerve cell), or in a plurality of neurons within a nerve bundle, or within a nerve (the combined signals of NAPs in a nerve bundle or nerve are referred to as a compound nerve action potential (CNAP)). Applying an optical signal (e.g., a short relatively high-power pulse of infrared (IR) laser light, for example at a signal wavelength about 1.9 microns) is another way to stimulate a NAP.

U.S. patent application Ser. No. 12/018,185 filed Jan. 22, 2008, titled "Hybrid Optical-Electrical Probes" by Mark P. Bendett and James S. Webb, which is incorporated herein by reference in its entirety (and which issued as U.S. Pat. No. 7,883,536 on Feb. 8, 2011), describes an optical-signal vestibular-nerve stimulation device and method that provides different nerve stimulation signals to a plurality of different vestibular nerves, including at least some of the three semi-circular canal nerves and the two otolith organ nerves. In some embodiments described in that patent application, balance conditions of the person are sensed by the implanted device, and based on the sensed balance conditions, varying infrared (IR) nerve-stimulation signals are sent to a plurality of the different vestibular nerves. Also described is a method that includes obtaining light from an optical source; transmitting the light through an optical fiber between a tissue of an animal and an optical transducer, and detecting electrical signals using conductors attached to the optical fiber. The application also describes an apparatus that includes an optical source, an optical transmission medium operatively coupled to the optical source and configured to transmit light from the optical source to respective nerves of each of one or more organs of an animal, an electrical amplifier, and an electrical transmission medium integral with the optical transmission medium and operatively coupled to the electrical amplifier, wherein the electrical transmission medium is configured to transmit an electrical signal from the respective nerves to the electrical amplifier.

One way to treat deafness in a person is to implant a cochlear-stimulation device (frequently called a cochlear implant) that senses sound in the environment (e.g., using a microphone) and then generates a combination of different electrical signals in different locations in the person's cochlear inner-ear structure. Because it is difficult to confine the electric field of each one of a large number of separate electrical signals, each intended for a particular one of a large number of separate nerves, e.g., among those nerves that extend in the bundle from the cochlea into the brain (it is possible to generate CNAP responses in perhaps only sixteen different nerve pathways (channels)), this conventional approach can provide only a crude representation of normal hearing.

U.S. Pat. No. 6,921,413 issued Jul. 24, 2005 to Mahadevan-Jansen et al., titled "Methods and devices for optical stimulation of neural tissues," and U.S. patent application Ser. No. 11/257,793 filed Oct. 24, 2005 by Webb et al., titled "Apparatus and method for Optical Stimulation of Nerves and Other Animal Tissue," are each incorporated herein by reference in their entirety. Both of these describe optical stimulation of nerves in general.

U.S. Patent Application Publication No. US 2006-0161227, of Walsh et al., titled "Apparatus and Methods for Optical Stimulation of the Auditory Nerve," is incorporated herein by reference in its entirety. This application describes a cochlear implant placed in a cochlea of a living subject for stimulating the auditory system of the living subject, where the auditory system comprises auditory neurons. In one embodiment, the cochlear implant includes a plurality of light sources $\{L_i\}$, placeable distal to the cochlea, each light source being operable independently and adapted for generating an optical energy, $E_i$, wherein i=1, . . . , N, and N is the number of the light sources, and delivering means placeable in the cochlea and optically coupled to the plurality of light sources, $\{L_i\}$, such that in operation, the optical energies $\{E_i\}$ generated by the plurality of light sources $\{L_i\}$ are delivered to target sites, $\{G_i\}$, of auditory neurons, respectively, wherein the target sites $G_1$ and $G_N$ of auditory neurons are substantially proximate to the apical end and the basal end of the cochlea, respectively.

U.S. Patent Application Publication No. US 2005 0004627 titled "Auditory midbrain implant" filed by Peter Gibson et al. on Aug. 26, 2004 is incorporated herein by reference. This application describes an electrode array that is implantable within the inferior colliculus of the midbrain and/or other appropriate regions of the brain of an implantee and adapted to provide electrical stimulation thereto. The electrode array an elongate member having a plurality of electrodes mounted thereon in a longitudinal array. A delivery cannula for delivering the electrode array comprised of two half-pipes is also described.

There is a need for efficacious apparatus and methods for optically, or optically and electrically, stimulating auditory nerve and/or brain tissue in a living animal in order to generate a nerve action potential (NAP) in one neuron (nerve cell), or in multiple neurons within a nerve bundle or nerve (where the combined individual NAPs form a compound nerve action potential, or CNAP), or similar physiological response in the animal. Optical or electrical-and-optical stimulation of neurons can provide more precision in terms of stimulating a particular nerve pathway than is possible using only electrical stimulation.

BRIEF SUMMARY OF THE INVENTION

The present invention provides an apparatus and a method for optically, or optically and electrically, stimulating neurons (e.g., auditory neurons) in the brainstem or midbrain (e.g., central auditory system) and/or brain tissue of a living animal (e.g., a human) to obtain a physiological response in the animal (e.g., a sense of hearing). In some embodiments, the simultaneous application of both an optical stimulation signal and an electrical stimulation signal provides more efficacious generation of NAP responses in the animal than either optical or electrical stimulation alone. In addition, the much higher precision possible when using optical stimulation permits many more channels of auditory nerve pathways to be individually and distinctly stimulated than is possible using electrical stimulation alone. In some embodiments, the application of an electrical field before or during the application of the optical stimulation pulse permits more reliable generation of nerve-action-potential signals than is possible using the optical signal pulse alone, and permits reliable generation of NAP signals.

One purpose of the present auditory-brainstem and -midbrain optical stimulator or hybrid stimulator (wherein the hybrid stimulator uses both optical and electrical stimulation) is to provide auditory sensations for patients who are otherwise deaf (and who are not, or may not be, candidates for cochlear implants due to injured or absent auditory nerves (for example, patients with neurofibromatosis type 2, cochlear ossification and/or labyrinthitis ossificans, severe cochlear hypoplasia, traumatic bilateral auditory nerve injury and the like). Another use of some embodiments of the present invention is to provide an apparatus and method for conducting basic and clinical research on how to improve the performance of auditory brainstem implants (ABIs)) using infrared laser technology, optionally also using simultaneous electrical stimulation. The optical auditory-brainstem or -midbrain stimulator can also be used as a powerful research tool to stimulate discrete regions and neuronal populations without the concerns of shock artifact, a phenomenon that is inherent to electrical-stimulation paradigms.

In some embodiments, the present invention provides apparatus and methods for optical stimulation or optical-and-electrical stimulation of auditory nerve pathways and/or brain tissue. Peripheral neural stimulation using infrared lasers has been demonstrated in several systems; however, to the inventors' knowledge, optical stimulation of the central nervous system (CNS) has not been previously described. In some embodiments of the present invention, radiant energy exposure of the cochlear nucleus using a mid-wavelength infrared laser generates optically-evoked auditory brainstem responses (oABRs). In one experiment, the cochlear nuclei of adult male Sprague-Dawley rats were exposed using a suboccipital craniotomy approach. Different regions of left cochlear nucleus were acutely stimulated, using a 200- or 400-μm-diameter (depending on the embodiment) optical fiber placed on the surface of the brainstem, with 50-μs to 750-μs pulses of 1849-nm-wavelength to 1865-nm-wavelength radiation at a rate of 10 Hz to 40 Hz and power levels ranging from 10% to 80% of a 5-W maximum power. oABRs were recorded during the period of optical stimulation. Post-experiment histology was performed to assess the extent of any tissue damage to the brainstem.

oABRs were observed during surface exposure of the cochlear nucleus to infrared radiation. Reproducible oABRs were seen at radiant energy levels (1849 nm) as low as 30% of a 5-W maximum power (i.e., 1.5 watts), with a 150-μs pulse width, and 10 Hz pulse repetition rate. No thermal tissue damage was seen in the cochlear nucleus following these acute experiments when pulse widths were less than 1 ms and power levels did not exceed 80% of a 5-W maximum power (i.e., 4 watts).

In other embodiments, the present invention provides apparatus and methods for optical stimulation or optical-and-electrical stimulation of nerve pathways and/or brain tissue of sensory modalities other than audition. In some such embodiments, apparatus and methods are provided for optical stimulation or optical-and-electrical stimulation of nerve pathways and/or brain tissue involved in vision. In other such embodiments, apparatus and methods are provided for optical- or optical-and-electrical stimulation of nerve pathways and/or brain tissue involved in olfaction. In other such embodiments, apparatus and methods are provided for optical- or optical-and-electrical stimulation of nerve pathways and/or brain tissue involved in balance. In other such embodiments, apparatus and methods are provided for optical- or optical-and-electrical stimulation of nerve pathways and/or brain tissue involved in tactile sense. In other such embodiments, apparatus and methods are provided for optical- or optical-and-electrical stimulation of nerve pathways and/or brain tissue involved in taste.

In some embodiments, one or more of the apparatus as described in the related provisional patent applications, patent applications and/or patents incorporated by reference above (e.g., Ser. Nos. 61/147,073, 60/872,930, 60/884,619, 60/885,879, 60/964,634, 61/015,665, 61/102,811, 11/257, 793, 11/536,639, 11/948,912, 11/536,642, 11/971,874, 12/018,185, 12/191,301, and 12/573,848) are used to generate and/or deliver the optical-stimulation signals and optionally the electrical-stimulation signals that are delivered to the brainstem or the midbrain of the patient using methods and apparatus of the present invention.

This is the first known description of optical stimulation of the CNS in an in vivo model. Mid-wavelength infrared lasers are capable of generating oABRs during acute stimulation of the cochlear nucleus without tissue damage and may provide the basis for novel auditory brainstem implant stimulation paradigms in the future.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1C is a schematic side view of implantable fiber-optic bundle 103 with optional electrical conductors.

FIG. 1D is a schematic end view of implantable fiber-optic bundle 103 with optional electrical conductors.

FIG. 2A is a graph 201 of 500-sample averages of electrical responses showing the effect of different power levels of the optical stimulation pulses, in a first rat subject.

FIG. 2B is a graph 202 of 100-, 200-, and 500-sample averages of electrical responses showing the effect of different numbers of samples of the optical stimulation pulses, in the first rat subject.

FIG. 3A is a graph 301 of 200-sample averages of electrical responses showing the effect of different pulse widths of the optical stimulation pulses, in the first rat subject.

FIG. 3B is a graph 302 of 200-sample averages of electrical responses showing the effect of different pulse rates of the optical stimulation pulses, in the first rat subject.

FIG. 8A is a graph 801 of electrical responses showing the effect of different pulse powers of 0.25-millisecond pulse widths at 20 pulses per second of 1849-nm-wavelength optical stimulation pulses, in the third rat subject.

FIG. 8B is a graph 802 of electrical responses showing the effect of different pulse powers of 0.15-millisecond pulse widths at 20 pulses per second of 1849-nm-wavelength optical stimulation pulses, in the third rat subject.

FIG. 8C is a graph 803 of electrical responses showing the effect of different pulse widths of at 20 pulses per second of 1849-nm-wavelength optical stimulation pulses, in the third rat subject.

FIG. 11 is a graph 1101 of electrical responses showing the effect of the animal being dead versus alive, in the third rat subject.

DETAILED DESCRIPTION OF THE INVENTION

Figure 1A:
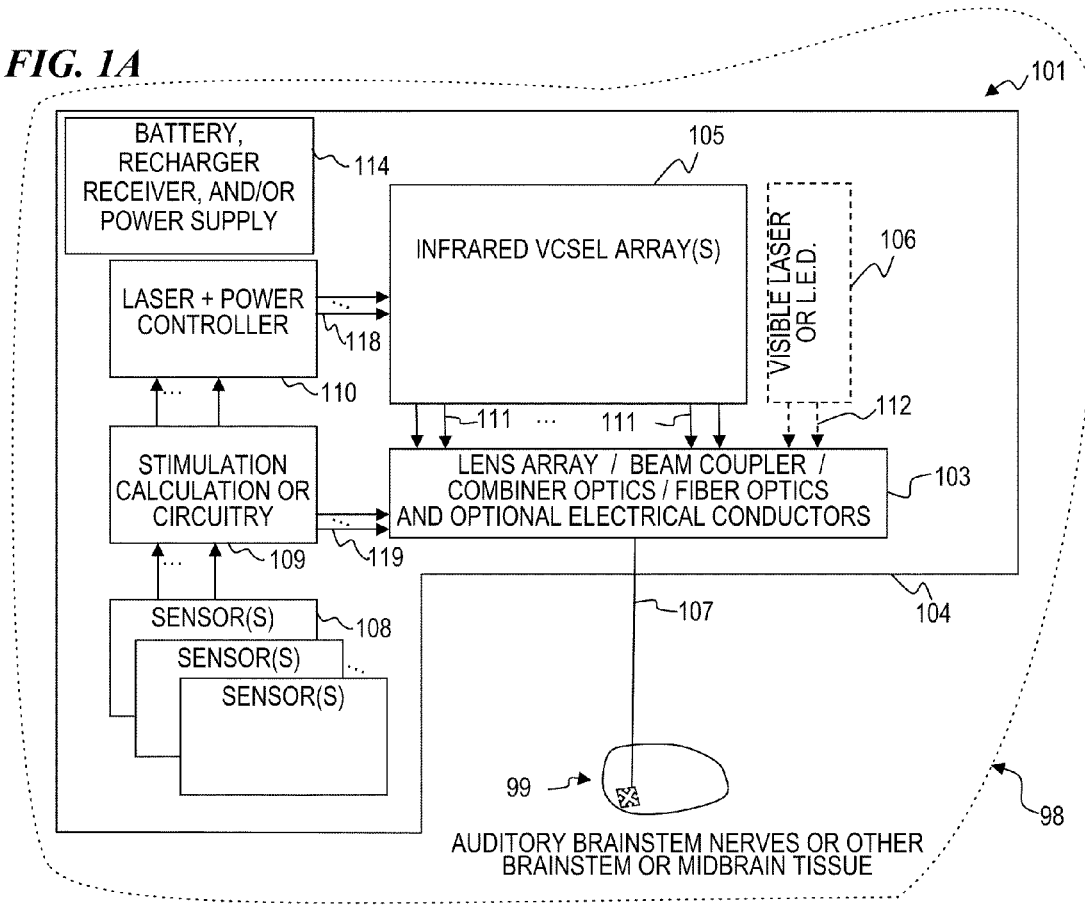
FIG. 1A is a block diagram of an implantable/partially implantable system 101.

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon, the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

The present invention uses a light-propagating transmission medium to carry optical signals between a light source and the tissue (e.g., neurons) of the patient, in order to stimulate a nerve action potential. In some embodiments, the transmission medium includes one or more optical fibers (e.g., a bundle of optical fibers, each of which includes a waveguide (e.g., the core of the fiber, which has a higher index of refraction than the cladding). In some embodiments, the light-propagating medium includes a plurality of side-by-side longitudinal (parallel-like) waveguides formed in an optical fiber or optical "ribbon". In some embodiments, a planar substrate is used, wherein the planar substrate includes a plurality of waveguides, and optionally includes other optical components such as filters, evanescent couplers, optical-fiber interfaces, selective gates that control the amplitude of light output, focusing elements, light-output ports (e.g., gratings that allow light to exit the waveguides toward the tissues of interest) and the like. In some embodiments, a tapered silicon substrate is used, the substrate having a plurality of waveguides formed by three-dimensional (3D) etching at the light-output tip (and optionally also at an input interface that receives light (e.g., from a plurality of optical fibers). In some embodiments, the output end of such an optical element is called a "probe" and allows a large number of light-output ports, such that after implantation adjacent to the brainstem or midbrain of the patient, individual ones of the output ports are individually activatable to determine which ports stimulate which nerve pathways. A mapping of which port is coupling light to which nerve pathway is then programmed into the controller that drives a particular optical signal to the desired nerve pathway to be stimulated. Because there are many more light-output ports than nerve destinations, the implanted device can be programmed to send the appropriate signals to each of a plurality of nerve pathways, greatly simplifying placement of the output probe (as compared to having to individually place each of a plurality of separate fibers). Further, at a later time, the implanted device can be recalibrated, remapped and reprogrammed to compensate for movement of the probe relative to the tissue to be stimulated. In addition, refinements based on later-discovered principles can be reprogrammed into the implanted device to provide a better sense of hearing for audio implants. Of course, other embodiments include implanted devices that provide other sensations, such as vision, olfaction, touch (some embodiments including sexual sensations), temperature, pressure, and the like.

In some embodiments, the light signal used to stimulate a nerve action potential includes wavelengths in the range of 1800 nm to 2100 nm. In other embodiments, the stimulation light signal includes wavelengths in the range of 1400 nm to 1500 nm, the range of 1500 nm to 1600 nm, or other suitable light wavelength in the range of 300 nm to 10,000 nm.

FIG. 1A is a block diagram of an implantable or partially implantable system 101 (according to some embodiments of the present invention) that uses a VCSEL (vertical-cavity surface-emitting laser) array for light stimulation of neuronal tissue 99 in the brainstem and/or midbrain nerves such as the auditory brainstem to obtain an auditory brainstem response (ABR) (e.g., some embodiments use a VCSEL array such as described by U.S. Provisional Patent Application No. 60/964,634 filed Aug. 13, 2007, titled "VCSEL Array Stimulator Apparatus and Method for Light Stimulation of Bodily Tissues"). System 101 represents one embodiment of the present invention, wherein a low-power, low-threshold VCSEL array 105 emits laser light from each of a plurality of VCSELs, for example VCSELs implemented as an array of separately activatable lasers formed in a monolithic semiconductor chip. Each laser beam is separately controlled by laser-and-power controller 110 that drives the laser-diode VCSELs under control of a processor or circuitry 109 that generates signals 111 that are configured to stimulate the tissue as desired. For example, in some embodiments, the light signals 111 are collimated, focused and/or guided by optics 103 within device enclosure 104 into delivery medium 107 (e.g., a bundle of optical fibers), which extends from the enclosure 104 to a remote location such as in the brainstem or midbrain 99 of patient 98. In some embodiments, the system also uses a visible laser and/or LED array 106 that produce visible light signals 112 to help align the VCSEL laser array signals 111 with the lens array/beam coupler/combiner optics 103, and/or to indicate where the IR signals are being emitted from the far end of delivery medium 107 to help the surgeon align the distal tip of the delivery medium 107 to the appropriate neuronal tissue during the implantation procedure. In some embodiments, one or more sensors 108 are used to obtain audio information, balance or orientation information, temperature information, or other information that is to be converted to nerve-stimulation signals (e.g., optical signals and optionally also electrical signals) to deliver to patient 98 through the patient's brainstem or midbrain neurons 99. In some embodiments, the sensors 108 are implanted inside the patient 98. In other embodiments (such as described below for FIG. 1B), one or more sensors are part of an external unit 120 that is wirelessly coupled to the implanted device 102.

In some embodiments, electrical nerve-stimulation signals 119 are generated by stimulation-calculation processor or circuitry 109, and are delivered to the stimulation site using delivery medium 107 (e.g., a bundle having one or more electrical conductors and one or more optical fibers), such as described in U.S. patent application Ser. No. 12/018,185 filed Jan. 22, 2008, titled "Hybrid Optical-Electrical Probes" (which issued as U.S. Pat. No. 7,883,536 on Feb. 8, 2011); U.S. patent application Ser. No. 12/191,301 filed Aug. 13, 2008, titled "VCSEL Array Stimulator Apparatus and Method for Light Stimulation of Bodily Tissues", and U.S. patent application Ser. No. 12/573,848 filed Oct. 5, 2009, titled "Nerve Stimulator and Method using Simultaneous Electrical and Optical Signals"(which issued as U.S. Pat. No. 8,160,696 on Apr. 17, 2012); each of which is incorporated herein by reference in its entirety.

In some embodiments, the electrical signals 119 are used to sensitize the neuronal tissue (as opposed to being sufficient to trigger a nerve action potential using only the electrical signal) in order that a lower-power optical stimulation signal is sufficient to trigger the desired nerve action potential (NAP) in one or more neurons in the brainstem or midbrain of the patient.

In some embodiments, the optical (and optional electrical) signals are delivered and directed upon the auditory brainstem nerves, i.e., Cranial Nerve VIII (the cranial nerve for hearing and balance), or other brainstem or midbrain tissue 99 of a patient 98. In some embodiments, some or all of system 101 is implanted within patient 98. In some embodiments, the end of delivery medium 107 that is distal to beam combiner 103 includes a plurality of optical fibers that are configured to output light in a plurality of different locations and/or different directions from a single location. In some embodiments, delivery medium 107 also includes a plurality of electrical conductors that are configured to output electrical signals in a plurality of different locations (e.g., to one or more of those locations at any one time) and/or different directions (e.g., to one or more of those directions at any one time) from a single location. In some embodiments, the electrical signals are used to precondition the neurons to be stimulated such that a lower-intensity optical signal can be used to trigger the desired nerve-action-potential pulse.

In some embodiments, the optical (and optional electrical) signals are delivered and directed upon other brainstem nerves, for instance, Cranial Nerve II (the cranial nerve for vision), Cranial Nerve I (the cranial nerve for olfaction), or the like. In some such embodiments, suitable external sensors 108 for the necessary input data (such as, for example, microphones, pressure sensors, vibration sensors, gyroscopes, accelerometers, gravity-direction sensors, electromagnetic-radiation sensors such as imaging devices, light sensors and color sensors, chemical sensors (i.e., for odors and/or taste), and the like).

Thus, in some embodiments, an imaging device is used as a sensor 108 (or as part of an external sensor-transmitter 120 as described below for FIG. 1B) to obtain image data, this image data is processed to detect vision aspects of the image data such as patterns (e.g., vertical objects, horizontal objects, diagonal objects, curved objects and the like), color (e.g., hue, saturation, brightness, contrast and the like with regard to various objects and patterns), motion (direction, speed, enlargement, and the like) and the processed image data is used to generate stimulation signals used to drive optical and/or electrical probes that stimulate the midbrain or brainstem portion of Cranial Nerve II (the cranial nerve for vision) in order to provide a simulated vision sensation for the patient. In some embodiments, electromagnetic-radiation sensors that do not generate image data as such, for example light sensors and color sensors, are used to obtain more generic electromagnetic-radiation data from the environment (such as the color of an object), and this generic electromagnetic-radiation data is processed to provide optical- and/or electrical-stimulation signals that stimulate the midbrain or brainstem portion of Cranial Nerve II to provide more fundamental sensations (such as the color of whatever the color sensor is aimed at).

Further, in some embodiments, one or more chemical sensors are used to obtain chemical data (e.g., data relating to gasses or particulates from the atmosphere, or materials such as salts, sugars and the like dissolved in a liquid), this chemical data is processed to detect odor aspects of the chemical data, and the processed odor data is used to generate stimulation signals used to drive optical and/or electrical probes that stimulate the midbrain or brainstem portion of Cranial Nerve I (the cranial nerve for olfaction) in order to provide a simulated smell and/or taste sensation for the patient.

Yet further, in some embodiments, one or more pressure, texture, vibration, weight and/or similar sensors are used to obtain touch-and-feel data, this touch-and-feel data is processed to detect mechanical-touch aspects of an object, and the processed mechanical-touch data is used to generate stimulation signals used to drive optical and/or electrical probes that stimulate the midbrain or brainstem portion of other nerve pathways in order to provide a simulated touch-and-feel sensation for the patient.

Still further, in some embodiments, one or more nerve-action-potential (NAP) sensors are used to obtain nerve-and-movement-disorder data, this nerve-and-movement-disorder data is processed to detect nerve-signal patterns that are indicative of Parkinson's Disease or other movement disorders, and the processed nerve-signal data is used to generate stimulation signals used to drive optical and/or electrical probes that stimulate the midbrain or brainstem portions (such as the red nucleus and substantia nigra) of affected nerve pathways in order to treat or inhibit the movement disorder of the patient.

In some embodiments, and as used herein and as used in the attached Figures and graphs, 100% power is 5 watts, and this delivers a pulse energy of 5 mJ in a 1-ms pulse. Thus, in FIG. 2A, a 100% power level (5 watts) delivered in 3-ms pulses is delivering 15 mJ per pulse, an 80% power level (4 watts) delivered in 3-ms pulses is delivering 12 mJ per pulse, a 60% power level (3 watts) delivered in 3-ms pulses is delivering 9 mJ per pulse, a 40% power level (2 watts) delivered in 3-ms pulses is delivering 6 mJ per pulse, and a 20% power level (1 watt) delivered in 3-ms pulses is delivering 3 mJ per pulse. Thus, 100% of 5 watts in a 3-millisecond pulse delivers 15 mJ per pulse energy. Similarly, in FIG. 2B, 80% of the 5-W power (i.e., 4 watts) in a 0.75-ms pulse delivers 3.0 mJ per pulse.

In some embodiments, long-wavelength VCSEL devices and/or VCSEL arrays, such as described in U.S. Pat. Nos. 7,031,363 and 7,004,645 (which are each incorporated herein by reference), are used for the VCSEL array 105.

With VCSEL emitters as small as about ten (10) microns (or smaller) in diameter per channel, in some embodiments, a single VCSEL chip or assembly is used to output multiple independent stimulation channels (VCSEL laser signals) in any array permutation or shape, and in some embodiments, these channels are fiber coupled, and/or direct light directly, to a plurality of areas of tissue. In some embodiments, a combination of both fiber-coupled and direct-propagation laser output is used to stimulate tissue.

Figure 1B:
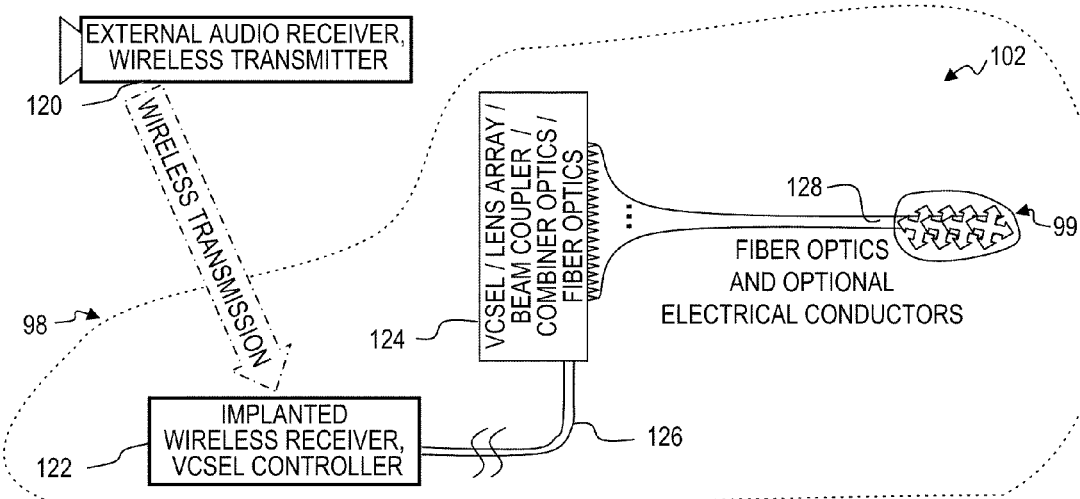
FIG. 1B is a block diagram of a wireless-transmission partially implantable system 102.

FIG. 1B is a block diagram of a wireless-transmission partially implantable system 102 that uses a VCSEL array for light stimulation of brainstem and/or midbrain neurons and/or organs 99 such as the auditory brainstem to obtain an auditory brainstem response (ABR). In some embodiments, system 102 is substantially similar to system 101 described above, except that one or more external sensors, computer processing devices and wireless-transmitter circuitry 120 replace or supplement one or more of the sensors 108. For example, in some embodiments, the external sensors include an audio receiver (such as a microphone), an auditory processor that converts frequencies and intensities of sounds into information that is wirelessly transmitted (for example using radio waves or other suitable means) to an implanted receiver, wherein the transmitted information is useful for generating optical (and optionally electrical) pulses that are used to stimulate neurons 99 of patient 98). In some embodiments, system 102 represents one embodiment of the present invention wherein a low-power, low-threshold VCSEL array 124 emits laser light from each of a plurality of VCSELs, for example VCSELs implemented as an array of separately activatable lasers formed in a monolithic semiconductor chip. Each laser beam is separately controlled by laser-and-power controller 122 that drives the set of laser-diode VCSELs, which together are configured to stimulate the tissue as desired. For example, in some embodiments, the light signals are collimated, focused and/or guided by optics into delivery medium 128 (e.g., a bundle of optical fibers). In some embodiments, the system also uses a visible laser and/or LED array (such as array 106 described above) that produce visible light signals to help align the VCSEL laser array signals with the lens array/beam coupler/combiner optics.

FIG. 1C is a schematic side view and FIG. 1D is a schematic end view, respectively, of an implantable fiber-optic bundle device 103 with optional electrical conductors 136 and 137. In some embodiments, implantable fiber-optic bundle 103 includes a plurality of radially positioned fiber-optic cables (e.g., a bundle of optical fibers around a central axis) 132, 133, 134 and 138. In some embodiments, a first set or tier (i.e., an innermost bundle) of optical fibers 132 are arranged radially around a central axis and terminates using angled facets (i.e., angled to direct light in a plurality of different outward angles from the central axis of the bundle of fibers) at the distal end of fiber-optic device 103. The angled facets are configured to each direct light from one or more core regions within each fiber 132 at a different radial (or radial-and-longitudinal) direction than the light coming from other fibers 132. In some embodiments, each fiber is configured to emit light outward from one end of the central axis of fiber-optic device 103 such that a different unique or limited set of one or more nerve fibers is stimulated by optical pulses emitted from each one of the angled end facets of the respective fibers. In some embodiments, device 103 is oriented such that the central axis of device 103 is substantially parallel to the length direction of the nerve bundle that is to be stimulated.

In some embodiments, the device 193 is implanted into a patient 98, and optical pulses are sent out one fiber at a time in order to identify which fiber evokes which sensation or response (such as the perception of a particular frequency caused by nerve pulses of a particular nerve, nerve axon, or the like). Once it has been determined which optical fiber evokes which response or sensation, the electronics portion 131 is configured or its software is programmed to send pulses at a calculated rate to cause the patient to sense the desired sensation (e.g., in some embodiments, to "hear" a voice having a complex mix of frequencies and intensities, the patient must receive nerve pulses (compound nerve action potentials, or CNAPs) at certain rates from certain nerve pathways, and device 103 would transmit optical signals (or a combination of optical and electrical signals) to cause the particular set of nerves to experience the CNAPs necessary for that "hearing" (or other sensation), which, for example, could be based on processing a microphone-received audio signal and generating a corresponding set of optical pulses at given repetition rates that are delivered through a selected set of optical fibers).

In some embodiments, a second set or tier of optical fibers 133 are arranged around the central axis radially further out and around the outer circumference of fiber-optical fibers 132, and each optical fiber 133 terminates using an outward-angled facet spaced at a short distance (leftward in FIG. 1C), e.g., at 500 microns (0.5 mm), 1 mm, 1.5 mm, 2 mm or other suitable distance from the distal end (the right-hand end in FIG. 1C) of fiber-optic bundle 103. In some embodiments, a third set or tier of optical fibers 134 are arranged around the central axis and radially further out and around the outer circumference of optical fibers 132 and optical fibers 133, and each optical fiber 134 terminates using an outward-angled facet spaced at a short distance (further leftward in FIG. 1C), e.g., at 1000 microns (1 mm), 1.5 mm, 2 mm, 2.5 mm, 3 mm or other suitable distance from the distal end (the right-hand end in FIG. 1C) of the fiber-optic bundle of device 103. In some embodiments, yet another set of optical fibers 138 are arranged around the central axis and optical fibers 132, optical fibers 133 and optical fibers 134 (i.e., optical fibers 138 surround optical fibers 134, optical fibers 134 surround optical fibers 133, optical fibers 133 surround optical fibers 132 and optical fibers 132 are arranged radially around the central axis). In some embodiments, each optical fiber 138 terminates using an outward-angled facet spaced at a short distance (still further leftward in FIG. 1C), e.g., at 1500 microns (1.5 mm), 2 mm, 2.5 mm, 3 mm, 3.5 mm, 4 mm or other suitable distance from the distal end (the right-hand end in FIG. 1C) of the fiber-optic bundle of device 103. Thus, in some embodiments, the ends of the fiber-optic cables 134 extend a distance beyond the ends of fiber-optic cables 138, the ends of the fiber-optic cables 133 extend a distance beyond the ends of fiber-optic cables 134 and the ends of the fiber-optic cables 132 extend a distance beyond the ends of fiber-optic cables 133 such that light emitted by each faceted end is not obstructed by surrounding fiber-optic cables and reaches a different portion of nerve tissue.

In some embodiments, the plurality of optical fibers 132, 133, 134 and 138 include faceted ends (e.g., cleaved or polished ends), wherein the face or facet of each faceted end of the plurality of optical fibers 132, 133, 134 and 138 points in a different radially-outward and longitudinally angled direction with respect to the central axis such that light emitted from each faceted end (e.g., 135 and 139) travels in a direction that is at least partially radially outward from the central axis and intersects a different nerve or set of nerve pathways.

In some embodiments, fiber-optic bundle 103 includes a plurality of electrical conductors 136 and 137. In some embodiments, one or more of the electrical conductors include a central conducting core (e.g., a bio-compatible metal or alloy) surrounded by an insulating material (e.g., a bio-compatible polymer, glass, enamel or other suitable insulator. In some embodiments, electrical conductor 136 is a single insulated wire that is arranged at the central axis of the plurality of fiber-optic cables 132, 133, 134 and 138 and the end of electrical conductor 136 is flush with or extends a short distance (e.g., 500, 1000, or 1500 microns) beyond the end of fiber-optic cables 132. In some embodiments, electrical conductors 137 include a plurality of insulated wires (or metallic-coated optical fibers or the like) arranged radially around or within the outer plurality of fiber-optic cables 138 and the ends of the electrical conductors 137 are arranged such that fiber-optic cables 138 are co-terminus or extend past the ends of the electrical conductors 137. In some embodiments, controller 131 generates signals or electrical current flows from one electrical conductor of the plurality of electrical conductors 137 to a second and different electrical conductor of the plurality of electrical conductors 137 (i.e., in a direction tangent to the optical-fiber bundle). In some embodiments, electrical current flows from one or more electrical conductors of the plurality of electrical conductors to the single electrical conductor 136 (i.e., in a longitudinal direction relative to the optical-fiber bundle or relative to one side of the optical-fiber bundle of device 103). In some embodiments, the electrical conductors are formed as a conducting layer (e.g., a metallization layer) that is deposited directly on each of one or more of the optical fibers 138, 134, and/or 133, and then covered (except at an exposed conductive probe (e.g., near the tip of the optical fiber)) with one or more insulating layers (hybrid electro-optic fibers such as described in U.S. patent application Ser. No. 12/018,185 filed Jan. 22, 2008, titled "Hybrid Optical-Electrical Probes", which is incorporated herein by reference, and which issued as U.S. Pat. No. 7,883,536 on Feb. 8, 2011).

In some embodiments, a combination of electrical signal(s) and optical signal(s) is used to generate the desired response (e.g., a CNAP in each of one or more nerve pathways at a repetition rate or time sequence chosen or calculated to generate a given sensation for the patient). In some embodiments, an external sensor (such as one or more microphones) is used to gather information about the environment (e.g., an audio signal based on received sounds, a video signal based on received images, or information from a gyroscope sensor, tilt sensor, temperature sensor, chemical or odor sensors or the like), which information is optionally processed external to the patient, and the resulting data is wirelessly transmitted (e.g., using radio waves) to an implanted device 103 internal to the patient. Thus, in some embodiments, a sensation of hearing is obtained using device 103. In other embodiments, other sensations such as balance, vertigo or the avoidance of vertigo, tilt, vision, touch, smell, or other sensation is obtained using device 103, wherein the given sensor(s) are collecting sensory data and device 103 is generating the corresponding sensation, depending on the location where the ends of the optical fibers (or bundle of optical fibers) and optionally electrical conductors are delivering the optical signals and optionally the electrical signal(s) or pre-conditioning stimulus. In other embodiments, a motor response (rather than a sensation) of the patient is obtained, such as an eye or tongue movement. By implanting the light-emitting end of the optic-fiber bundle of device 103 in or along motor nerves of the spinal cord or peripheral nerve system, other motor responses (muscle contractions) may be obtained.

In some embodiments, the optical-fiber bundle end of device 103 is situated in or along the brainstem (the medulla, pons and/or midbrain), or along the cranial nerves, or even in or along side of the higher brain centers such as the cerebral cortex. In some embodiments, the optical-fiber bundle end of device 103 is situated in or along the spinal cord of the patient, further from the brain than the brainstem. In some embodiments, the optical-fiber bundle end of device 103 is situated in or along the limbic system (e.g., thalamus, hypothalamus, amygdala, and/or hippocampus), or the pituitary gland, cerebellum, or corpus callosum.

The human brain has twelve pairs of special nerves called the cranial nerves. These are specific bundles of neurons and axons which transmit special information to and from the brain, without going through the spinal cord. The cranial nerves each provide highly specific functions (sensory or motor). The cranial nerves all exit from the bottom of the brain and brainstem and exit the skull through various foramina to reach their sources or targets. In some embodiments, the optical-fiber-bundle light-delivery (and optionally electrical-stimulation) end of device 103 is situated in or along one or more of the cranial nerves to obtain one or more of the following responses of Table 1:

TABLE 1

| CRANIAL NERVE | NAME | MAIN FUNCTION |
|---|---|---|
| Cranial Nerve I | Olfactory Nerve | Smell |
| Cranial Nerve II | Optic Nerve | Vision |
| Cranial Nerve III | Oculomotor Nerve | Eye movement |
| Cranial Nerve IV | Trochlear Nerve | Eye movement |
| Cranial Nerve V | Trigeminal Nerve | Facial sensation |
| Cranial Nerve VI | Abducens Nerve | Eye movement |
| Cranial Nerve VII | Facial Nerve | Facial movement |
| Cranial Nerve VIII | Auditory Nerve | Hearing and balance |
| Cranial Nerve IX | Glossopharyngeal Nerve | Organs and Taste |
| Cranial Nerve X | Vagus Nerve | Organs and Taste |
| Cranial Nerve XI | Accessory Nerve | Shoulder shrug & head turn |
| Cranial Nerve XII | Hypoglossal Nerve | Tongue movement |

In some embodiments, the present invention provides a method for stimulating neurons (central or peripheral projections) of an auditory brainstem or midbrain of a patient to provide auditory sensations for the patient. This method includes delivering light signals to a plurality of neurons of the auditory brainstem or midbrain of the patient.

In some embodiments, the delivering of light signals includes delivering the light signals to peripheral projections of the neurons. In some embodiments, the delivering of light signals includes delivering the light signals to central portions of the neurons.

In some embodiments, the delivering of light signals includes delivering infrared light from a laser. In some embodiments, the delivering of light signals includes delivering infrared light from a VCSEL.

Some embodiments further include delivering an electrical signal to a plurality of neurons of the auditory brainstem or midbrain of the patient.

In some embodiments, the delivering of the light signals includes obtaining a plurality of light signals from one or more laser light sources and delivering the obtained light signals to discrete portions of excitable tissues, wherein the responses triggered by the light signals are interpretable by the patient's brain as sensory responses.

In some embodiments, the delivering of the light signals further includes selectively controlling the light signals to optically stimulate the neurons in order to control nerve action potentials (NAPS) produced by the one or more nerves. In some embodiments, the selectively controlling the light signals includes controlling a pulse width of the plurality of light signals. In some embodiments, the selectively controlling the light signals includes controlling a pulse repetition rate of the plurality of light signals. In some embodiments, the selectively controlling the light signals includes controlling a pulse shape of the plurality of light signals. In some embodiments, the selectively controlling the light signals includes controlling a DC background amount of light intensity of the plurality of light signals. In some embodiments, the selectively controlling the light signals includes controlling a precharge amount of light intensity followed by a trigger amount of light intensity of the plurality of light signals. In some embodiments, the selectively controlling the light signals includes controlling the light signals to increase a frequency of the NAPS produced by the one or more nerves that would otherwise occur without the plurality of light signals.

In some embodiments, the method further includes applying a precharge current of electrical energy that is followed by a trigger amount of pulsed light intensity of the plurality of light signals.

In some embodiments, the obtaining the plurality of light signals includes implanting a self-contained battery-powered laser-light-generation device and obtaining the plurality of light signals from the battery-powered laser-light-generation device.

In some embodiments, the delivering the plurality of light signals to the plurality of neurons of the auditory brainstem or midbrain includes positioning a delivery end of one or more fibers against one or more neurons of the auditory brainstem or midbrain and using one or more optical fibers to guide the light signals from a laser source to the one or more neurons.

In some embodiments, the one or more laser light sources include a first light source and a second light source, wherein the selectively controlling the plurality of light signals includes controlling the first light source to send a first series of pulses during a first period of time and controlling the second light source to send a second series of pulses during the first period of time, and wherein the first series of pulses differs from the second series of pulses in repetition rate.

Some embodiments further include sensing one or more conditions that affect balance, and wherein the selectively controlling the plurality of light signals to the brainstem or midbrain includes controlling the light signals, at least partly based on the sensed one or more conditions that affect balance, to provide a sense-of-balance nerve stimulation. In some such embodiments, the sensing of the one or more conditions that affect balance includes monitoring eye movements.

Some embodiments further include sensing one or more sounds, and wherein the selectively controlling the plurality of light signals includes controlling the light signals to the brainstem or midbrain, at least partly based on the sensed sounds, to provide a sense-of-hearing nerve stimulation.

In some embodiments, the present invention provides a method that includes obtaining a plurality of light signals from one or more laser light sources; delivering the plurality of light signals to a plurality of nerve pathways in the brainstem or midbrain of a living animal; and selectively controlling the plurality of light signals to optically stimulate the plurality of nerve pathways in order to control nerve action potentials (NAPS) produced by the plurality of nerve pathways. In some embodiments, the plurality of nerve pathways in the brainstem or midbrain includes auditory nerve pathways. In some embodiments, the plurality of nerve pathways in the brainstem or midbrain includes sense-of-balance nerve pathways.

In some embodiments, the living animal is a human person. In some embodiments, the living animal is a large non-human animal, e.g., a race horse or dairy cow. In some embodiments, the living animal is a small non-human animal, e.g., a dog, cat, rodent or the like.

In some embodiments, the selectively controlling the light signals includes controlling a pulse width of the plurality of light signals.

In some embodiments, the selectively controlling the light signals includes controlling a duty cycle of the plurality of light signals.

In some embodiments, the selectively controlling the light signals includes controlling an on-time and an off-time of the plurality of light signals.

In some embodiments, the selectively controlling the light signals includes controlling a wavelength of the plurality of light signals.

In some embodiments, the selectively controlling the light signals includes controlling a pulse repetition rate of the plurality of light signals.

In some embodiments, the selectively controlling the light signals includes controlling a pulse shape of the plurality of light signals.

In some embodiments, the selectively controlling the light signals includes controlling a minimum light intensity and a maximum light intensity of the plurality of light signals.

In some embodiments, the present invention provides a combination of electrical and optical stimulation.

In some embodiments, the selectively controlling the light signals includes controlling a DC background amount of light intensity of the plurality of light signals.

In some embodiments, the present invention provides a combination of electrical and optical stimulation. In some embodiments, the method further includes selectively controlling and applying to one or more tissues of the animal one or more electrical signals (i.e., hybrid electrical and optical stimulation of one or more tissues). In some embodiments, the selectively controlling and applying the electrical signal(s) includes controlling and applying a DC background amount of electrical signal. In some embodiments, the selectively controlling and applying the electrical signal(s) includes applying electrical pulses.

In some embodiments, the selectively controlling the light signals includes controlling a precharge amount of light intensity followed by a trigger amount of light intensity of the plurality of light signals.

In some embodiments, the selectively controlling the light signals includes controlling the light signals to delay at least some of the NAPs produced by the one or more nerves that would otherwise occur without the plurality of light signals.

In some embodiments, the selectively controlling the light signals includes controlling the light signals to increase a frequency of the NAPs produced by the one or more nerves that would otherwise occur without the plurality of light signals.

In some embodiments, the selectively controlling the light signals includes controlling the light signals to decrease a frequency of the NAPs produced by the one or more nerves that would otherwise occur without the plurality of light signals.

In some embodiments, the obtaining the plurality of light signals includes implanting a self-contained battery-powered laser-light-generation device.

In some embodiments, the plurality of light signals includes implanting self-contained infrared (IR) laser device.

In some embodiments, the delivering the plurality of light signals to one or more nerves of each of one or more inner-ear vestibular organs includes using one or more optical fibers to guide the light signals.

In some embodiments, the delivering the plurality of light signals to one or more nerves of each of one or more inner-ear vestibular organs includes positioning a delivery end of one or more fibers against a vestibular organ and using the one or more optical fibers to guide the light signals from a laser source to the vestibular organ.

In some embodiments, the one or more laser light sources include a first light source and a second light source, wherein the selectively controlling the plurality of light signals includes controlling the first light source to send a first series of pulses during a first period of time and controlling the second light source to send a second series of pulses during the first period of time, and wherein the first series of pulses differs from the second series of pulses in repetition rate.

In some embodiments, the present invention provides a method further including sensing one or more conditions that affect balance, and wherein the selectively controlling the plurality of light signals includes controlling the light signals, at least partly based on the sensed one or more conditions that affect balance, to provide a sense-of-balance nerve stimulation.

In some embodiments, the sensing of the one or more conditions that affect balance includes sensing motion and orientation.

In some embodiments, the sensing the one or more conditions that affect balance includes monitoring muscular stimulation.

In some embodiments, electrical stimulation delivered via nerves connected to muscles is sensed. In some embodiments, the result of the muscular movement is sensed.

In some embodiments of the invention, monitoring muscular stimulation includes monitoring eye movements.

In some embodiments, electrical stimulation delivered via nerves connected to eye muscles is sensed. In some embodiments, the eye movement is sensed to indirectly sense eye muscle stimulation.

In some embodiments, the present invention provides an apparatus that includes one or more laser light sources configured to generate a plurality of light signals; and a transmission medium configured to transmit the plurality of light signals from the one or more laser light sources to one or more nerves of each of one or more inner-ear vestibular organs of a living animal; a controller to selectively control the plurality of light signals from each of the one or more infrared-laser light sources such that the light signals provide controlled optical stimulation to the one or more nerves in order to control nerve action potentials (NAPS) produced by the one or more nerves.

In some embodiments, the living animal is a human person. In some embodiments, the living animal is a large non-human animal, e.g., a race horse or dairy cow. In some embodiments, the living animal is a small non-human animal, e.g., a dog or cat.

In some embodiments, the control of the light signals provided by the controller includes selective control of a pulse width of the plurality of light signals.

In some embodiments, the control of the light signals provided by the controller includes selective control of a duty cycle of the plurality of light signals.

In some embodiments, the control of the light signals provided by the controller includes selective control of an on-time and an off-time of the plurality of light signals.

In some embodiments, the control of the light signals provided by the controller includes selective control of a wavelength of the plurality of light signals.

In some embodiments, the control of the light signals provided by the controller includes selective control of a pulse repetition rate of the plurality of light signals.

In some embodiments, the control of the light signals provided by the controller includes selective control of a pulse shape of the plurality of light signals.

In some embodiments, the control of the light signals provided by the controller includes selective control of a minimum light intensity and a maximum light intensity of the plurality of light signals.

In some embodiments, the control of the light signals provided by the controller includes selective control of a DC background amount of light intensity of the plurality of light signals.

In some embodiments, the control of the light signals provided by the controller includes selective control of a pre-charge amount of light intensity followed by a trigger amount of light intensity amount of light intensity of the plurality of light signals.

In some embodiments, the control of the light signals provided by the controller includes selective control of the plurality of light signals to delay at least some of the NAPs produced by the one or more nerves that would otherwise occur.

In some embodiments, the control of the light signals provided by the controller includes selective control of the plurality of light signals to increase a frequency of the NAPs produced by the one or more nerves that would otherwise occur.

In some embodiments, the control of the light signals provided by the controller includes selective control of the plurality of light signals to decrease a frequency of the NAPs produced by the one or more nerves that would otherwise occur.

In some embodiments, the apparatus includes an implanted a self-contained battery-powered laser light-generation device.

In some embodiments, the obtaining the plurality of light signals includes implanting self-contained infrared (IR) laser device.

In some embodiments, the a transmission medium configured to transmit light signals from the one or more laser light sources to one or more nerves of each of one or more inner-ear vestibular organs of a living animal includes one or more optical fibers configured to guide the light signals.

In some embodiments, the one or more laser light sources include a first light source and a second light source, wherein the control of the light signals provided by the controller includes selective control of the first light source to send a first series of pulses during a first period of time and selective control of the second light source to send a second series of pulses during the first period of time, and wherein the first series of pulses differs from the second series of pulses in repetition rate.

In some embodiments, the present invention provides an apparatus further including at least one sensor configured to sense one or more conditions that affect balance, and wherein the control of the light signals provided by the controller includes selective control of the light signals to provide a sense-of-balance nerve stimulation at least partly based on a signal from the at least one sensor.

In some embodiments, the at least one sensor includes a motion sensor.

In some embodiments, the at least one sensor includes an orientation sensor.

In some embodiments, the at least one sensor includes a muscular stimulation monitor.

In some embodiments, electrical stimulation carried via efferent nerves to muscles is sensed. In some embodiments, the result of the muscular movement is sensed.

In some embodiments, the muscular stimulation monitor includes a sensor that monitors eye movements.

In some embodiments, the present invention provides an apparatus that includes means for obtaining a plurality of light signals from one or more laser light sources; means for delivering the plurality of light signals to one or more nerve pathways of each of one or more inner-ear vestibular organs of a living animal; and means for selectively controlling the plurality of light signals to optically stimulate the one or more nerves in order to control nerve action potentials (NAPS) or compound nerve-action potentials (CNAPs) produced in the one or more nerve pathways.

In some embodiments, the living animal is a human person. In some embodiments, the living animal is a large non-human animal, e.g., a race horse or dairy cow. In some embodiments, the living animal is a small non-human animal, e.g., a dog or cat.

In some embodiments, the means for selectively controlling the light signals includes means for controlling a pulse width of the plurality of light signals.

In some embodiments, the means for selectively controlling the light signals includes means for controlling a duty cycle of the plurality of light signals.

In some embodiments, the means for selectively controlling the light signals includes means for controlling an on-time and an off-time of the plurality of light signals.

In some embodiments, the means for selectively controlling the light signals includes means for controlling a wavelength of the plurality of light signals.

In some embodiments, the means for selectively controlling the light signals includes means for controlling a pulse repetition rate of the plurality of light signals.

In some embodiments, the means for selectively controlling the light signals includes means for controlling a pulse shape of the plurality of light signals.

In some embodiments, the means for selectively controlling the light signals includes means for controlling a minimum light intensity and a maximum light intensity of the plurality of light signals.

In some embodiments, the means for selectively controlling the light signals includes means for controlling a DC background amount of light intensity of the plurality of light signals.

In some embodiments, the means for selectively controlling the light signals includes means for controlling a pre-charge amount of light intensity followed by a trigger amount of light intensity of the plurality of light signals.

In some embodiments, the means for selectively controlling the light signals includes means for controlling the light signals to delay at least some of the NAPs produced by the one or more nerves that would otherwise occur without the plurality of light signals.

In some embodiments, the means for selectively controlling the light signals includes means for controlling the light signals to increase a frequency of the NAPs produced by the one or more nerves that would otherwise occur without the plurality of light signals.

In some embodiments, the means for selectively controlling the light signals includes means for controlling the light signals to decrease a frequency of the NAPs produced by the one or more nerves that would otherwise occur without the plurality of light signals.

In some embodiments, the means for obtaining the plurality of light signals includes implanting a self-contained battery-powered laser-light-generation device.

In some embodiments, the obtaining the plurality of light signals includes implanting self-contained infrared (IR) laser device.

In some embodiments, the means for delivering the plurality of light signals to one or more nerves of each of one or more inner-ear vestibular organs includes using one or more optical fibers to guide the light signals.

In some embodiments, the one or more laser light sources include a first light source and a second light source, wherein the means for selectively controlling the plurality of light signals includes means for controlling the first light source to send a first series of pulses during a first period of time and means for controlling the second light source to send a second series of pulses during the first period of time, and wherein the first series of pulses differs from the second series of pulses in repetition rate.

In some embodiments, the present invention provides an apparatus further including means for sensing one or more conditions that affect balance, and wherein the means for selectively controlling the plurality of light signals includes means for controlling the light signals, at least partly based on the sensed one or more conditions that affect balance, to provide a sense-of-balance nerve stimulation.

In some embodiments, the means for sensing of the one or more conditions that affect balance includes means for sensing motion and orientation.

In some embodiments, the means for sensing the one or more conditions that affect balance includes means for monitoring muscular stimulation.

In some embodiments, electrical stimulation delivered via nerves connected to muscles is sensed. In some embodiments, the result of the muscular movement is sensed.

In some embodiments, the means for monitoring muscular stimulation includes means for monitoring eye movements.

In some embodiments, electrical stimulation delivered via nerves connected to eye muscles is sensed. In some embodiments, the eye movement is sensed to indirectly sense eye muscle stimulation.

In some embodiments, electrical stimulation to eye muscles is sensed. In some embodiments, the eye movement is sensed to indirectly sense eye muscle stimulation.

In some embodiments, the present invention provides a method that includes obtaining light from an optical source; and transmitting the light to respective nerves of each of a plurality of inner-ear balance organs of an animal. The animal can either be a human or be some other animal.

In some embodiments, the transmitting includes transmitting different amounts of the light through optical fibers to stimulate respective nerves of each of the plurality of inner-ear balance organs.

In some embodiments, the transmitting includes transmitting different wavelengths of the light to stimulate respective nerves of each of the plurality of inner-ear balance organs.

In some embodiments, various parameters are adjusted and/or controlled, such as the pulse repetition rate or pattern, the pulse width, the pulse intensity, the wavelength(s), the amount of background constant (DC) optical level, and/or selected multiple simultaneous wavelengths. Multiple wavelengths are provided, in some embodiments, by using a plurality of lasers having different wavelengths. In some embodiments, a plurality of fibers is used to deliver the stimulation light to a plurality of stimulation sites.

In some embodiments, the present invention includes triggers and sensors that generate signals that are input to software of the present invention, wherein the software analyzes the signals and based on the analysis, generates control signals that control the parameters, such as frequency and intensity of light output (e.g., laser pulses) for each of one or more channels that communicate with the vestibular nucleus. For example, some embodiments use sensors such as described in U.S. Pat. No. 6,546,291 issued to Merfeld et al. on Apr. 8, 2003, which was described above and which is incorporated herein by reference. For example, some embodiments include sensors for detecting characteristics of the patient's head, eyes, posture and the like.

Some embodiments use one or more implanted VCSEL arrays to directly stimulate the desired nerves, while in other embodiments, one or more implanted VCSELs are optically coupled using one or more optical fibers leading to the stimulation sites.

In other embodiments, one or more VCSEL arrays are located external to the patient's body and use transcutaneous coupling to one or more implanted fiber arrays. In some embodiments, the implanted fiber arrays provide one or more feedback loops (e.g., a fiber having both of its ends facing outwards from the body) in order to assist coupling alignment. In some embodiments, permanent magnets are used on the implanted fiber arrays and external VCSEL stimulator to maintain coupling and assist in coupling alignment. In some embodiments, the implanted fiber arrays have a bulbous head on each fiber to collect and direct laser light into the fiber core.

Some embodiments provide programmable and/or reprogrammable control. In some embodiments, the controller is implanted in the body, and in some other embodiments, the controller is located external to the body and coupled to an implanted fiber array using transcutaneous coupling (e.g., some embodiments use a VCSEL array to provide light from the stimulator.

In some embodiments, electrical signals of the nerves are sensed and used to provide feedback to the controller, in order to better control the laser stimulation signal.

In some embodiments, the optical nerve stimulation is used to supplement or override the nerve responses generated by the inner ear organs. Some conditions, e.g., Benign Paroxysmal Positional Vertigo (BPPV), result from over-stimulation of nerves in a normally resting position. Through additional optical nerve stimulation, the natural nerve responses can be supplemented or overridden. In some embodiments, wider pulse width optical nerve stimulations are used to override or reduce the frequency of natural nerve responses to treat some inner ear conditions.

In some embodiments, the obtaining light includes implanting a self-contained infrared laser device.

In some embodiments, the obtaining light includes implanting a self-contained battery-powered device.

In some embodiments, the animal is a human person. In some embodiments, the animal is not human. Some embodiments further include sensing a condition that affects balance, and wherein the transmitting includes transmitting different light signals to each of a plurality of different balance-sense organs to provide the person sense-of-balance nerve stimulation.

In other embodiments, the present invention provides an apparatus that includes an optical source; and a transmission medium configured to transmit light from the optical source to respective nerves of each of a plurality of inner-ear balance organs of an animal.

In some embodiments, the transmission medium includes a plurality of optical fibers, and the optical source couples different amounts of the light through the plurality of optical fibers to stimulate different respective nerves of each of the plurality of inner-ear balance organs.

In some embodiments, the optical source couples different wavelengths of the light to stimulate different respective nerves of each of the plurality of inner-ear balance organs.

In some embodiments, the optical source includes a self-contained implantable infrared laser device.

In some embodiments, the optical source includes a self-contained battery-powered device.

In some embodiments, the animal is a human person. Some embodiments further include at least one sensor configured to sense a condition that affects balance, and wherein the transmission medium transmits different light signals, based on the sensed condition, to each of a plurality of different balance-sense organs to provide the person sense-of-balance nerve stimulation.

In other embodiments, the present invention provides an apparatus that includes means for obtaining light from an optical source; and means for transmitting the light to respective nerves of each of a plurality of inner-ear balance organs of an animal.

In some embodiments of the apparatus, the means for transmitting includes means for transmitting different amounts of the light through optical fibers to stimulate respective nerves of each of the plurality of inner-ear balance organs. In some embodiments, the means for transmitting includes means for transmitting different wavelengths of the light to stimulate respective nerves of each of the plurality of inner-ear balance organs. In some embodiments, the means for obtaining light includes a self-contained infrared laser implantable device. In some embodiments, the means for obtaining light includes a self-contained battery-powered implantable device.

In some embodiments, the animal is a human person, and the apparatus further includes means for sensing a condition that affects balance, and wherein the means for transmitting includes means for transmitting different light signals, based on the sensed condition, to each of a plurality of different balance-sense organs to provide the person sense-of-balance nerve stimulation.

For each of the above embodiments that describe a stimulation of a vestibular organ, there are other embodiments of the present invention that stimulate any and/or all elements of the vestibular system: inner-ear vestibular organs, cranial nerve VIII, vestibular nucleus, or any other central process of an animal's system.

Current conventional methods to excite neurons of the auditory brainstem or auditory midbrain include surface and penetrating electrodes that electrically stimulate surrounding neural tissue. The target of these electrodes is the cochlear nucleus or the inferior colliculus.

Some Relevant Publications are the Following:

Shannon R V, Otto S R.; Psychophysical measures from electrical stimulation of the human cochlear nucleus, Hear. Res., 1990 Aug. 1; 47(1-2):159-68.

Otto S R, House W E, Brickman D E, Heidelberger W E, Nelson R A.; *Auditory brain stem implant: effect of tumor size and preoperative hearing level on function*, Ann. Otol. Rhinol Laryngeal., 1990 October; 99(10 Pt 1):789-90.

Liu X, McPhee G, Seldon H L, Clark G M.; Histological and physiological effects of the central auditory prosthesis: surface versus penetrating electrodes, Hear, Res. 1997 December; 114(1-2):264-74.

Lenarz T, Lim H H, Reuter G, Patrick J F, Lenarz M.; The auditory midbrain implant: a new auditory prosthesis for neural deafness-concept and device description, Otol. Neurotol. 2006 September; 27(6):838-43. Review.

Samii A, Lenarz M, Majdani O, Lim H H, Samii M, Lenarz T.; Auditory midbrain implant: a combined approach for vestibular schwannoma surgery and device implantation. Otol. Neurotol. 2007 January; 28(1):31-8.

The cochlear nucleus is an important first relay station for all auditory information that originates in the ear and travels along the auditory nerve. This target is very small, however, and after conventional electrical auditory-brainstem-implant electrodes are placed, many patients experience non-auditory sensations because non-auditory neurons nearby are being stimulated. The fundamental advantage of optical stimulation is that only neurons that are located in the path of the radiant energy are excited, and so one can achieve far greater selectivity when targeting neural tissues optically rather than electrically. As a result, one could use many more point sources of stimulation (optical-signal fibers) and have enhanced channel selectivity using optical stimulation. This has inherent advantages in the auditory brainstem and midbrain because there are so many different (non-auditory) neurons in very close proximity to the auditory neurons. In some embodiments of the present invention, an optical auditory brainstem or midbrain implant, or a hybrid stimulator that uses both optical and electrical stimulation (either applied on the surface or when penetrated into the brainstem or midbrain), uses more stimulation channels (optical-signal fibers or electrical-signal electrodes) to provide improved auditory performance compared with a conventional electrical stimulator.

The following describes the inventors' first attempts to stimulate the auditory brainstem of an animal model of human hearing (rat cochlear nucleus) using surface application of radiant energy from an infrared laser source delivered using an optical fiber. These experiments involve: (1) anesthetizing the rat; (2) performing a tracheotomy; (3) exposing the left auditory brainstem (left cochlear nucleus); (4) delivering the laser optical fiber with a micromanipulator to contact the surface of the brainstem; (5) using software to trigger the laser, delivering focused radiant energy to the cochlear nucleus from a mid-wavelength infrared laser source (available from Lockheed Martin Aculight Corporation, Bothell, Wash., USA) while monitoring for electrical activity of the central auditory pathways (optically-evoked auditory brainstem responses, or oABRs). We are also performing experiments to focally stimulate the same regions of the auditory brainstem using a micro-bipolar electrode (electrically-evoked ABRs, or eABRs) to compare oABRs with eABRs. In some embodiments, a hybrid device that incorporates both optical and electrical stimulation may have clinical applications for future auditory-brainstem-implant (ABI) designs.

FIG. 2A is a graph 201 of 500-sample averages of electrical responses (signals from the nerve) showing the effect of different power levels of the optical stimulation pulses, in a first rat subject. The uppermost plot labeled "100%" represents 100% of a 5-watt optical signal (5 watts), the next-to-uppermost plot labeled "80%" represents 80% of a 5-watt optical signal (4 watts), the middle plot labeled "60%" represents 60% of a 5-watt optical signal (3 watts), the next-to-lowermost plot labeled "40%" represents 40% of a 5-watt optical signal (2 watts), and the lowermost plot labeled "20%" represents 20% of a 5-watt optical signal (1 watt). It appears that a 4-watt signal is sufficient to reliably trigger a nerve response, and that perhaps even 3-watt or even 2-watt signals may trigger a desired response.

FIG. 2B is a graph 202 of 100-, 200-, and 500-sample averages of electrical responses (signals from the nerve) showing the effect of different numbers of samples of the optical stimulation pulses, in the first rat subject.

FIG. 3A is a graph 301 of 200-sample averages of electrical responses (signals from the nerve) showing the effect of different pulse widths (durations) of the optical-stimulation pulses, in the first rat subject. It appears that a 1-millisecond-long or longer pulse signal (at an 80% level (4 watts)) is sufficient to reliably trigger a nerve response when using a pulse repetition rate of 13 pulses per second (13 pps).

FIG. 3B is a graph 302 of 200-sample averages of electrical responses showing the effect of different pulse rates of the optical stimulation pulses, in the first rat subject. It appears that a 1.5-millisecond-long pulse signal (at an 80% level (4 watts)) is sufficient to reliably trigger a nerve response when using a pulse repetition rates of 5 to 30 pulses per second (5-30 pps).

Figure 4A:
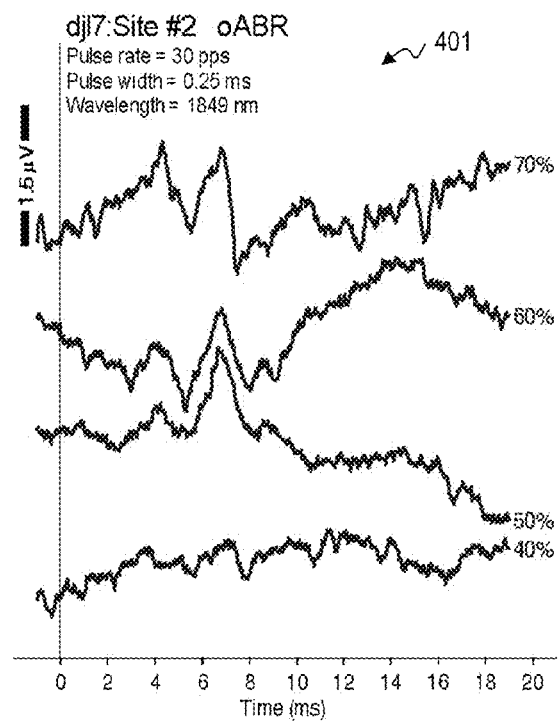
FIG. 4A is a graph 401 of electrical responses showing the effect of different pulse powers of 0.25-millisecond pulse widths at 30 pulses per second of 1849-nm-wavelength optical stimulation pulses, in a second rat subject.

FIG. 4A is a graph 401 of electrical responses showing the effect of different pulse powers of 0.25-millisecond pulse widths at 30 pulses per second of 1849-nm-wavelength optical stimulation pulses, in a second rat subject.

Figure 4B:
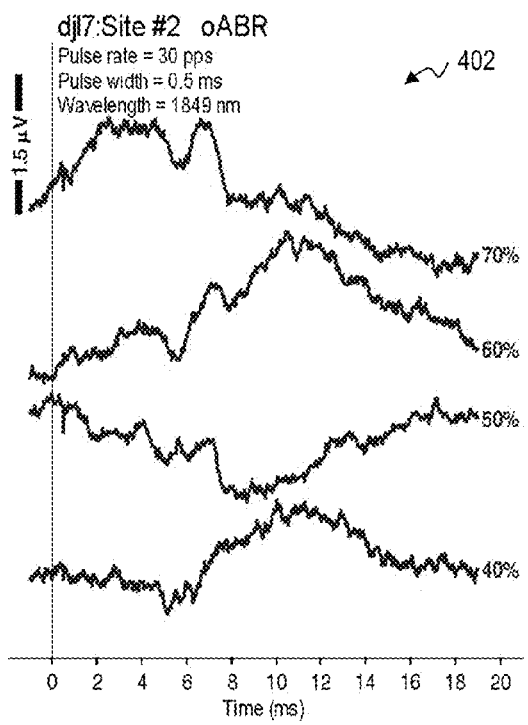
FIG. 4B is a graph 402 of electrical responses showing the effect of different pulse powers of 0.5-millisecond pulse widths at 30 pulses per second of 1849-nm-wavelength optical stimulation pulses, in the second rat subject.

FIG. 4B is a graph 402 of electrical responses showing the effect of different pulse powers of 0.5-millisecond pulse widths at 30 pulses per second of 1849-nm-wavelength optical stimulation pulses, in the second rat subject.

Figure 4C:
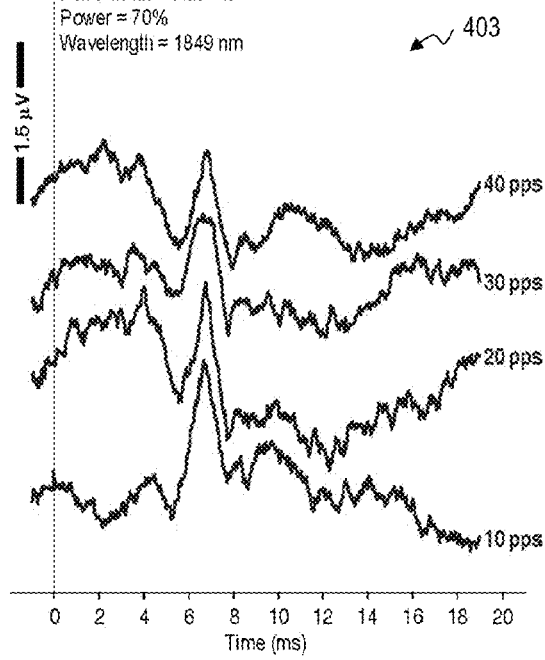
FIG. 4C is a graph 403 of electrical responses showing the effect of different pulse-repetition rates of 0.25-millisecond pulse widths of 1849-nm-wavelength optical stimulation pulses, in the second rat subject.

FIG. 4C is a graph 403 of electrical responses showing the effect of different pulse-repetition rates of 0.25-millisecond pulse widths of 1849-nm-wavelength optical stimulation pulses, in the second rat subject.

Figure 5A:
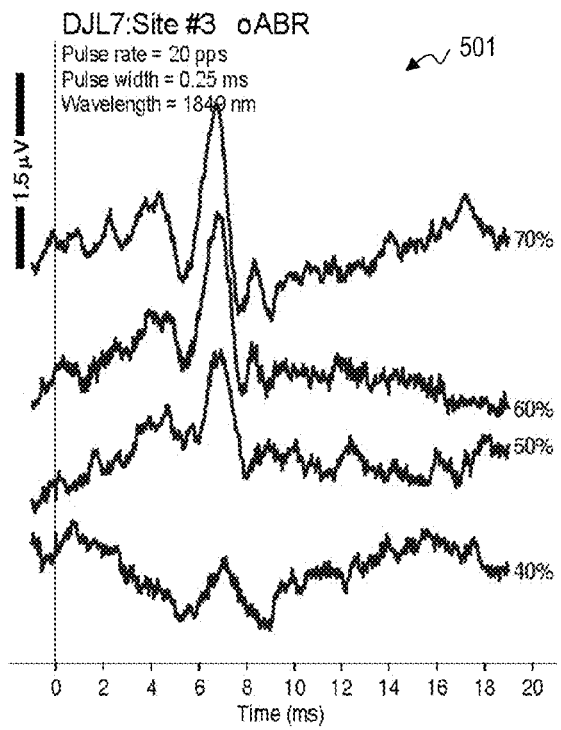
FIG. 5A is a graph 501 of electrical responses showing the effect of different pulse powers of 0.25-millisecond pulse widths at 20 pulses per second of 1849-nm-wavelength optical stimulation pulses, in the second rat subject.

FIG. 5A is a graph 501 of electrical responses showing the effect of different pulse powers of 0.25-millisecond pulse widths at 20 pulses per second of 1849-nm-wavelength optical stimulation pulses, in the second rat subject.

Figure 5B:
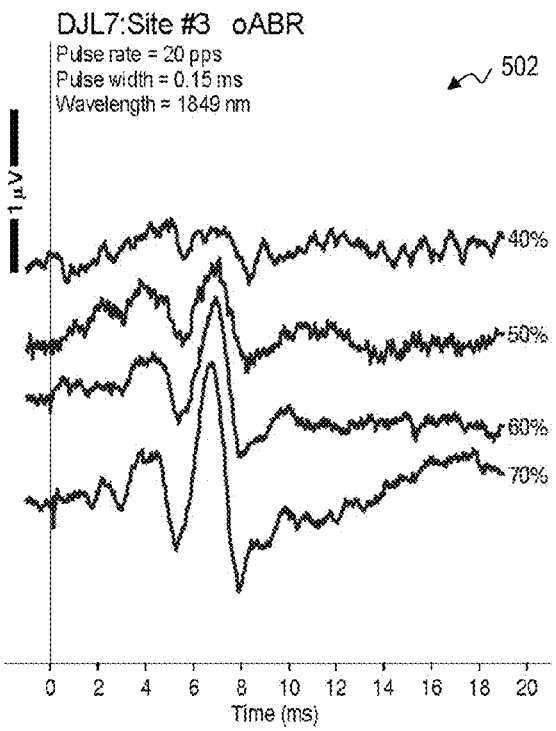
FIG. 5B is a graph 502 of electrical responses showing the effect of different pulse powers of 0.15-millisecond pulse widths at 20 pulses per second of 1849-nm-wavelength optical stimulation pulses, in the second rat subject.

FIG. 5B is a graph 502 of electrical responses showing the effect of different pulse powers of 0.15-millisecond pulse widths at 20 pulses per second of 1849-nm-wavelength optical stimulation pulses, in the second rat subject.

Figure 5C:
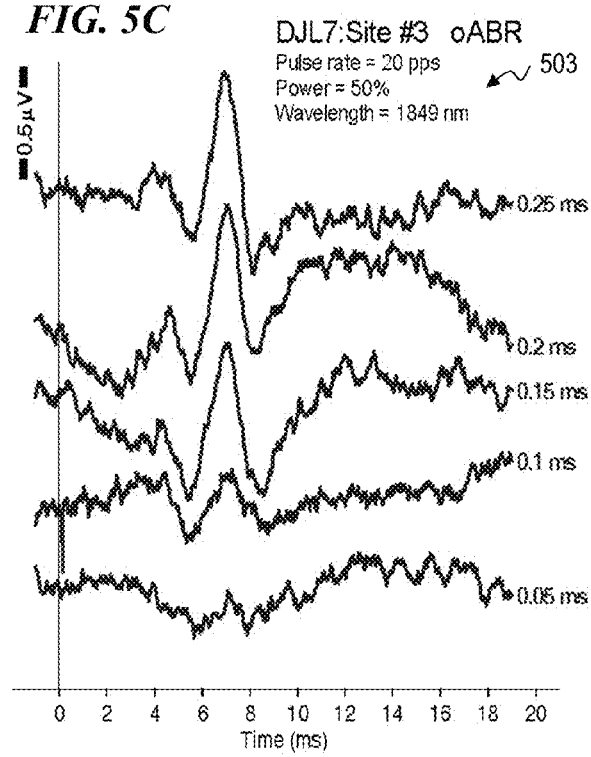
FIG. 5C is a graph 503 of electrical responses showing the effect of different pulse widths of at 20 pulses per second of 1849-nm-wavelength optical stimulation pulses, in the second rat subject.

FIG. 5C is a graph 503 of electrical responses showing the effect of different pulse widths of at 20 pulses per second of 1849-nm-wavelength optical stimulation pulses, in the second rat subject.

Figure 6:
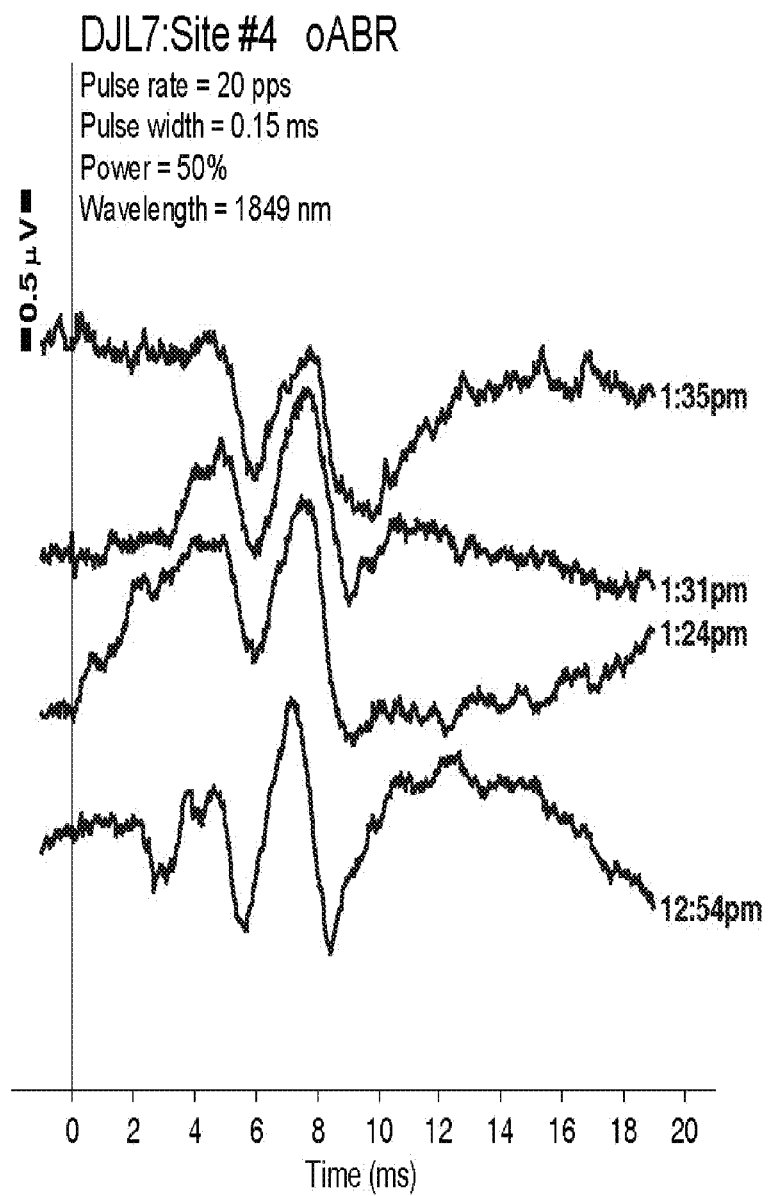
FIG. 6 is a graph 601 of electrical responses showing the effect of different amounts of time after start of stimulation of 0.15-millisecond pulse widths at 20 pulses per second of 1849-nm-wavelength optical stimulation pulses, in the second rat subject.

FIG. 6 is a graph 601 of electrical responses showing the effect of different amounts of time after start of stimulation of 0.15-millisecond pulse widths at 20 pulses per second of 1849-nm-wavelength optical stimulation pulses, in the second rat subject.

Figure 7A:
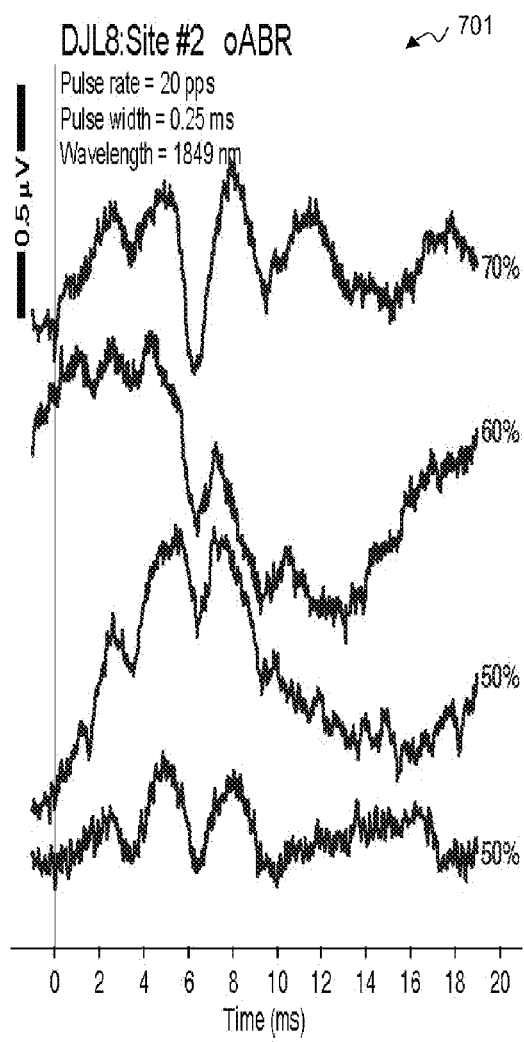
FIG. 7A is a graph 701 of electrical responses showing the effect of different pulse powers of 0.25-millisecond pulse widths at 20 pulses per second of 1849-nm-wavelength optical stimulation pulses, in a third rat subject.

FIG. 7A is a graph 701 of electrical responses showing the effect of different pulse powers of 0.25-millisecond pulse widths at 20 pulses per second of 1849-nm-wavelength optical stimulation pulses, in a third rat subject.

Figure 7B:
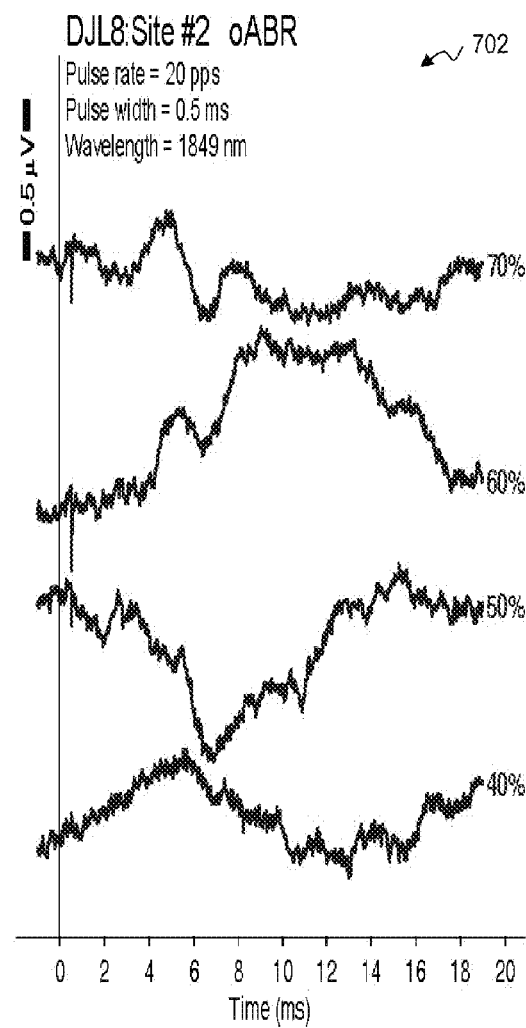
FIG. 7B is a graph 702 of electrical responses showing the effect of different pulse powers of 0.5-millisecond pulse widths at 20 pulses per second of 1849-nm-wavelength optical stimulation pulses, in the third rat subject.

FIG. 7B is a graph 702 of electrical responses showing the effect of different pulse powers of 0.5-millisecond pulse widths at 20 pulses per second of 1849-nm-wavelength optical stimulation pulses, in the third rat subject.

FIG. 8A is a graph 801 of electrical responses showing the effect of different pulse powers of 0.25-millisecond pulse widths at 20 pulses per second of 1849-nm-wavelength optical stimulation pulses, in the third rat subject.

FIG. 8B is a graph 802 of electrical responses showing the effect of different pulse powers of 0.15-millisecond pulse widths at 20 pulses per second of 1849-nm-wavelength optical stimulation pulses, in the third rat subject.

FIG. 8C is a graph 803 of electrical responses showing the effect of different pulse widths of at 20 pulses per second of 1849-nm-wavelength optical stimulation pulses, in the third rat subject.

Figure 9A:
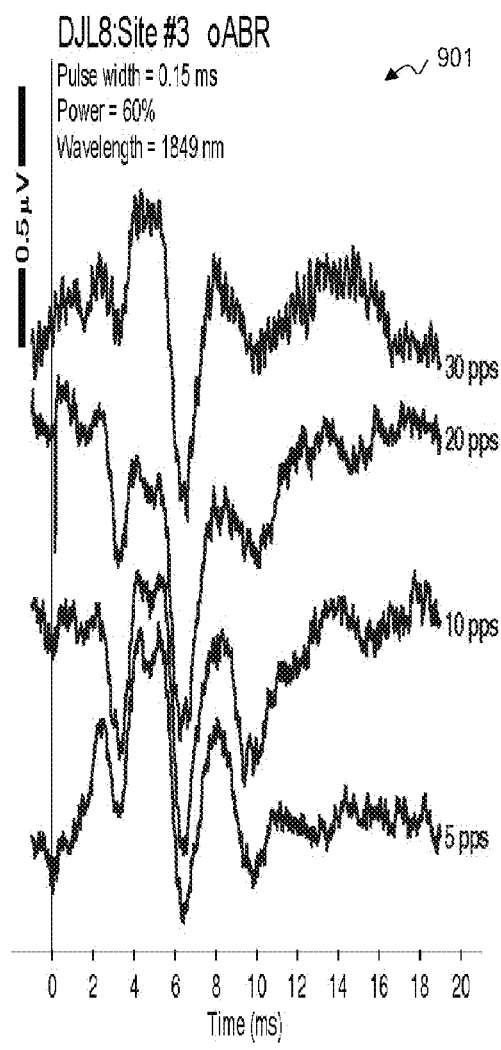
FIG. 9A is a graph 901 of electrical responses showing the effect of different pulse-repetition rates of 0.15-millisecond pulse widths of 1849-nm-wavelength optical stimulation pulses, in the third rat subject.

FIG. 9A is a graph 901 of electrical responses showing the effect of different pulse-repetition rates of 0.15-millisecond pulse widths of 1849-nm-wavelength optical stimulation pulses, in the third rat subject.

Figure 9B:
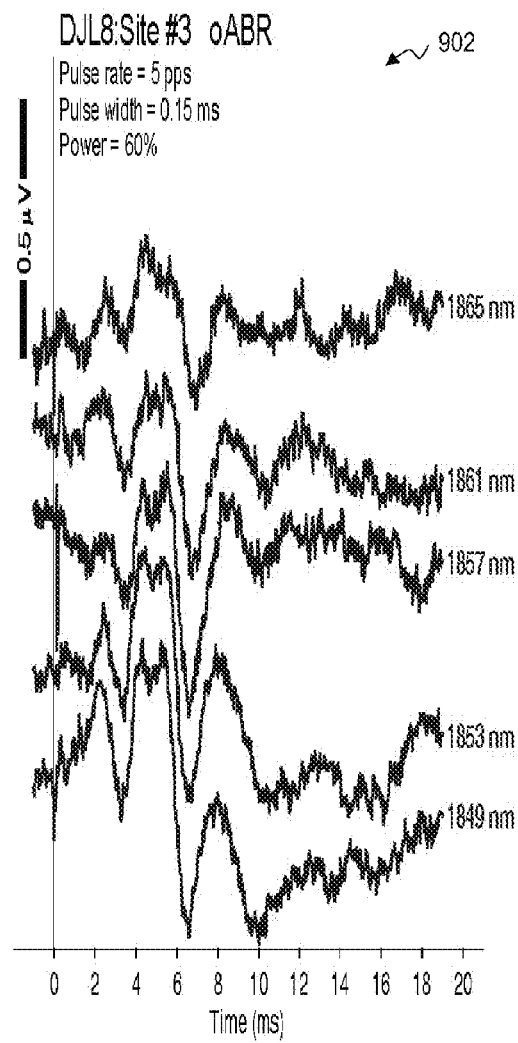
FIG. 9B is a graph 902 of electrical responses showing the effect of different optical-stimulation wavelengths rates of 0.15-millisecond pulse widths at a pulse-repetition rate (PRR) of 5-pulses-per-second optical stimulation, in the third rat subject.

FIG. 9B is a graph 902 of electrical responses showing the effect of different optical-stimulation wavelengths rates of 0.15-millisecond pulse widths at a pulse-repetition rate (PRR) of 5-pulses-per-second optical stimulation, in the third rat subject.

Figure 10A:
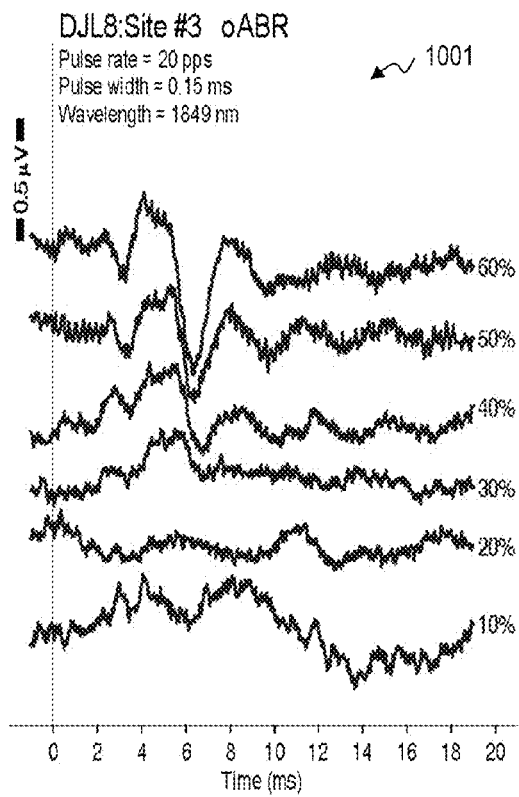
FIG. 10A is a graph 1001 of electrical responses showing the effect of different optical pulse powers of 0.15-millisecond pulse widths at 20 pulses per second of 1849-nm-wavelength optical stimulation pulses, in the third rat subject.

FIG. 10A is a graph 1001 of electrical responses showing the effect of different optical pulse powers of 0.15-millisecond pulse widths at 20 pulses per second of 1849-nm-wavelength optical stimulation pulses, in the third rat subject.

Figure 10B:
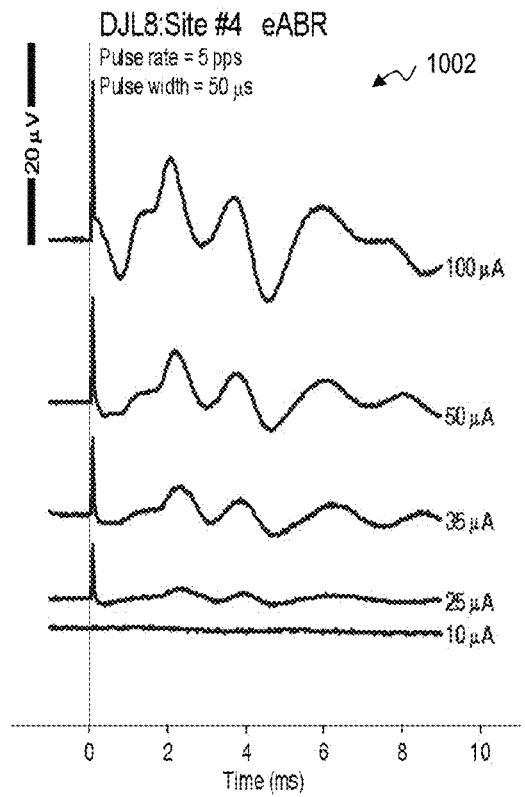
FIG. 10B is a graph 1002 of electrical responses showing the effect of different electrical pulse currents of 0.05-millisecond pulse widths at a PRR of 5 pulses per second of electrical stimulation, in the third rat subject.

FIG. 10B is a graph 1002 of electrical responses showing the effect of different electrical pulse currents of 0.05-millisecond pulse widths at a PRR of 5 pulses per second of electrical stimulation, in the third rat subject.

Figure 10C:
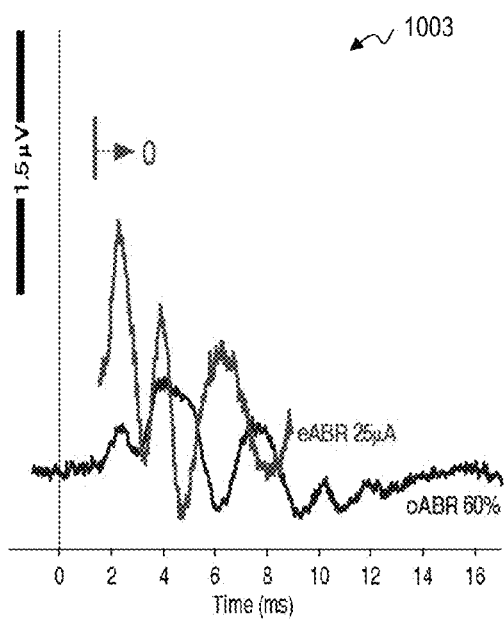
FIG. 10C is a graph 1003 of superimposed electrical responses showing a 0.0-millisecond delay of starting a 0.025-mA electrical-stimulation pulse at the same time as a 60% power optical-stimulation pulse, in the third rat subject.

FIG. 10C is a graph 1003 of superimposed electrical responses showing a 0.0-millisecond delay of starting a 0.025-mA electrical-stimulation pulse at the same time as a 60% power optical-stimulation pulse, in the third rat subject.

Figure 10D:
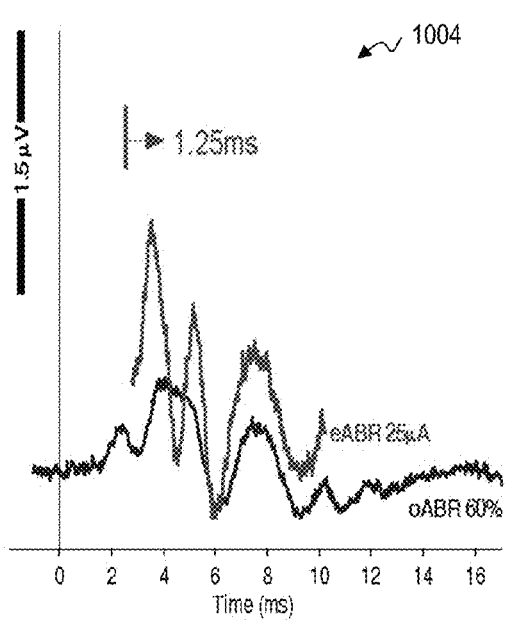
FIG. 10D is a graph 1004 of superimposed electrical responses showing a 1.25-millisecond delay of starting a 0.025-mA electrical-stimulation pulse after a 60% power optical-stimulation pulse, in the third rat subject.

FIG. 10D is a graph 1004 of superimposed electrical responses showing a 1.25-millisecond delay of starting a 0.025-mA electrical-stimulation pulse after a 60% power optical-stimulation pulse, in the third rat subject.

FIG. 11 is a graph 1101 of electrical responses showing the effect of the animal being dead versus alive, in the third rat subject.

Figure 12:
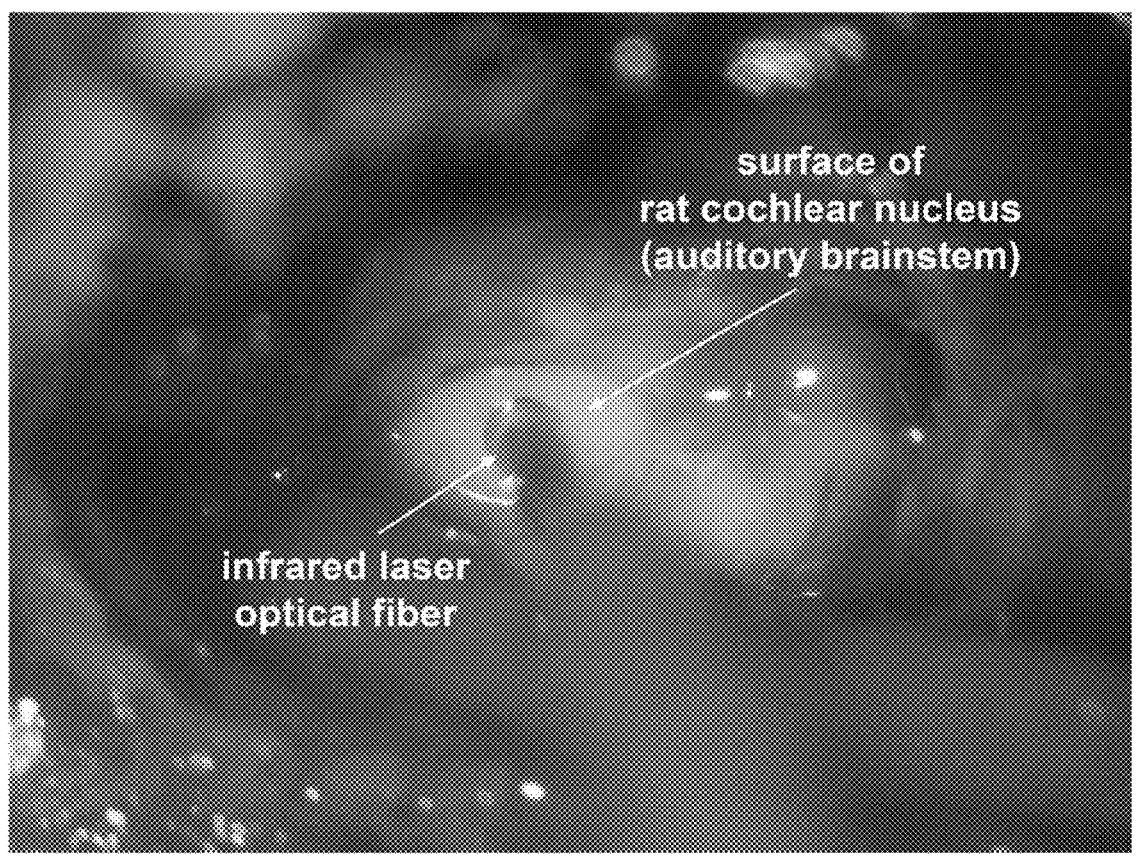
FIG. 12 is a photo micrograph 1201 of an optical fiber from an infrared laser implanted at the surface of a rat cochlear nucleus (auditory brainstem).

FIG. 12 is diagram 1201 from an intraoperative photo taken from one of our animal experiments demonstrating the technique of directly stimulating the central nervous system using laser energy from an optical fiber. Other figures show data from our first three rats (a rat for which the data are labeled DJL2 (FIG. 2A, FIG. 2B, FIG. 3A and FIG. 3B), a rat for which the data are labeled DJL7 (FIG. 4A, FIG. 4B, FIG. 4C, FIG. 5A, FIG. 5B, FIG. 5C and FIG. 6), and a rat for which the data are labeled DJL8 (FIG. 7A, FIG. 7B, FIG. 8A, FIG. 8B, FIG. 8C, FIG. 9A, FIG. 9B, FIG. 10A, FIG. 10B and FIG. 11), demonstrating the successful generation of oABRs using an infrared laser.

Some Advantages of the Invention Over Former Methods

One main advantage of optical stimulation of the auditory brainstem is the greater selectivity of neuronal activation using radiant energy compared with electrical stimulation. Only neurons in the path of the laser light are activated. Future optical-electrode hybrid designs will be able to use many more channels than electrically based systems, where channel crosstalk becomes a problem when using more electrodes spaced closely together. This will have implications for use not only in the auditory system but also for the development of the optical prosthesis, for example, and other peripheral and central stimulators. In addition, the target of stimulation in the auditory brainstem (either the cochlear nucleus or inferior colliculus) is small and there are many different neurons that are found in close proximity to the auditory neurons. In some embodiments, the greater precision seen with optical stimulation allows for more precise selective activation of particular central auditory neurons and minimizes the non-specific stimulation of surrounding non-auditory neurons such as the facial nerve. In contrast, unintended stimulation of non-auditory neurons is commonly seen in patients who have conventional auditory brainstem implants that simply rely on electrical stimulation alone.

Current conventional auditory brainstem implants rely on electrical stimulation and were approved by the Food and Drug Administration (FDA) in 2000. The present invention supplements or replaces such electrical stimulation with optical-electrical stimulation or just optical stimulation.

Current conventional auditory brainstem implants provide sound awareness but little to no speech understanding (except with lip-reading) in the vast majority of patients who have neurofibromatosis type 2 and have an ABI. Optical or optical-electrical hybrid in vivo stimulation of the auditory brainstem according to the present invention is an alternative approach to simulate the auditory system centrally and may result in improved performance in these patients.

The present invention is the first demonstration that stimulation of the central nervous system (in this case, the auditory system) is feasible using a mid-wavelength infrared laser. We have been able to stimulate central nervous system tissue using both surface and penetrating optical fiber applications and observe oABRs.

There are a number of peer-reviewed papers that describe the use of infrared stimulation of the cochlea, but to the inventors' knowledge none that describe the use of infrared lasers to stimulate the central nervous system in vivo.

A group from Vanderbilt University has described infrared laser stimulation in rat-brain slices (not in vivo) in a conference-proceedings publication, but this was not a peer-reviewed publication: Cayce, J M; Kao, C C; Mahadevan, G; Malphurus, J D; Konrad, P E; Jansen, E D; and Mahadevan-Jansen, A. *Optical stimulation of rat thalamocortical brain slices*. SPIE Proceedings January 2008, San Jose, Calif.

We have been able to successfully use infrared laser stimulation to generate optically-evoked ABRs in vivo using both surface and penetrating stimulation of the cochlear nucleus with an optical fiber in both a rat and guinea pig model.

In some embodiments, the present invention provides a method for stimulating neurons of a brainstem or midbrain of a patient to provide sensations for the patient. This method includes generating a plurality of light signals that, when applied to a neuron of a person, can stimulate a nerve action potential in the neuron; delivering the light signals to one or a plurality of neurons of the brainstem or midbrain of the patient; and selectively controlling the plurality of light signals to optically stimulate the one or more neurons in order to control nerve action potentials (NAPs) produced by the plurality of neurons. Some embodiments further include receiving (or measuring or sensing or obtaining) an audio signal; and processing the received audio signal to obtain frequency and intensity information, wherein the delivering of light signals comprises delivering the light pulses to an auditory portion of the brainstem or midbrain of the patient, and wherein the selectively controlling of the light signals includes selectively controlling the light signals to emit light pulses to selected locations of the brainstem or midbrain of the patient based on the frequency information and at selected pulse-repetition rates based on the intensity information. In some such embodiments, the method further includes delivering an electrical signal to the plurality of neurons of the auditory portion of the brainstem or midbrain of the patient, such that a combination of the electrical signal and the light signals stimulate the nerve action potentials in the plurality of neurons.

Some embodiments of the method further include further comprising sensing one or more conditions that affect balance, and wherein the selectively controlling the plurality of light signals includes controlling the light signals, at least partly based on the sensed one or more conditions that affect balance, to provide a sense-of-balance nerve stimulation to the brainstem or midbrain of the patient.

Some embodiments of the method further include receiving image data; and processing the received image data to obtain vision information, wherein the delivering of light signals comprises delivering the light pulses to a vision portion of the brainstem or midbrain of the patient.

In some embodiments of the method, the delivering of light signals further includes delivering infrared light from a laser.

In some embodiments of the method, the delivering of light signals further includes delivering infrared light from a vertical-cavity surface-emitting laser (VCSEL).

In some embodiments of the method, the delivering of light signals further includes delivering the light signals to peripheral projections of the neurons.

In some embodiments of the method, the delivering of light signals further includes delivering the light signals to central portions of the neurons.

In some embodiments of the method, the delivering of the light signals further includes obtaining a plurality of light signals from one or more laser light sources and delivering the obtained light signals to discrete portions of excitable tissues, said signals being interpretable by the patient's brain as sensory responses.

In some embodiments of the method, the delivering of the light signals further includes selectively controlling the light signals to optically stimulate the one or more neurons in order to control nerve action potentials (NAPs) produced by the one or more neurons. In some embodiments of the method, the selectively controlling the light signals further includes controlling a pulse width of the plurality of light signals. In some embodiments of the method, the selectively controlling the light signals further includes controlling a pulse repetition rate of the plurality of light signals. In some embodiments of the method, the selectively controlling the light signals further includes controlling a pulse shape of the plurality of light signals. In some embodiments of the method, the selectively controlling the light signals further includes controlling a DC background amount of light intensity of the plurality of light signals. In some embodiments of the method, the selectively controlling the light signals further includes controlling a precharge amount of light intensity followed by a trigger amount of light intensity of the plurality of light signals. In some embodiments of the method, the selectively controlling the light signals further includes controlling the light signals to increase a frequency of the NAPs produced by the one or more neurons that would otherwise occur without the plurality of light signals.

In some embodiments of the method, the obtaining of the plurality of light signals further includes implanting a self-contained battery-powered laser-light-generation device.

In some embodiments of the method, the delivering of the light signals to the plurality of neurons of the brainstem or midbrain of the patient includes positioning a delivery end of a plurality of optical fibers in a probe end placed against the brainstem or midbrain of the patient and using the plurality of optical fibers to guide the light signals from a laser source to the brainstem or midbrain of the patient.

In some embodiments of the method, the generating of the light signals includes providing a first laser source and a second laser source, wherein the selectively controlling the plurality of light signals includes controlling the first laser source to send a first series of pulses during a first period of time and controlling the second laser source to send a second series of pulses during the first period of time, and wherein the first series of pulses differs from the second series of pulses in repetition rate. In some embodiments of the method, the sensing of the one or more conditions that affect balance includes monitoring eye movements.

In some embodiments, the present invention provides an apparatus that includes one or more light sources that are configured to generate a plurality of light signals; a transmission medium configured to transmit the plurality of light signals from the one or more light sources to a plurality of neurons of a brainstem or midbrain of a living animal to provide auditory sensations for the living animal; and a controller operatively coupled to the one or more light sources to selectively control the plurality of light signals from each of the one or more light sources such that the light signals provide controlled optical stimulation to the plurality of neurons in order to control nerve action potentials (NAPs) produced by the plurality of neurons.

In some embodiments of the apparatus, control of the light signals provided by the controller includes selective control of a duty cycle of the plurality of light signals.

In some embodiments of the apparatus, the control of the light signals provided by the controller includes selective control of a wavelength of the plurality of light signals.

In some embodiments of the apparatus, the transmission medium includes a plurality of data channels (i.e., input and/or output channels (called "I/Os")). In some embodiments, the transmission medium includes a plurality of optical fibers, each having a conductive material (e.g., a metal film) applied to a surface of the optical fiber, wherein the conductive material is in turn covered with an insulator (e.g., a polymer coating, and/or a silicon oxide and/or silicon nitride insulator layer), and optionally one or more additional conductive layers further coated by additional insulator layers to provide a coaxially shielded electrical conductor that is formed directly on the optical fiber, and wherein the optical fiber is used to deliver the optical stimulation pulses and the one or more electrical conductors are used to transmit electrical stimulation or pre-conditioning electrical energy to the tissue being stimulated. In some embodiments, the electrical conductors are also used to carry electrical signals sensed from the neurons of the patient (e.g., NAP signals in the nerve pathways are detected electrically using the conductors formed on the optical fibers). In some embodiments, each of a plurality of the optical fibers have a metallic coating that has an insulator formed over the metallic coating, and a bundle of such fibers deliver a plurality of different optical signals (e.g., the optical-stimulation pulses are individually controlled) in parallel and a plurality of different stimulation electrical signals (e.g., the electrical-stimulation or -preconditioning pulses are individually controlled) in parallel such that different areas of the brainstem or midbrain of the patient are stimulated in different manners (e.g., different frequencies of sensed audio are used to calculate the various streams of pulse data (the streams being the time-sequenced pulses for each channel of data that are each sent to different respective nerve pathways (wherein the different nerve pathways each initially represent nerve signals for different frequencies, but it is believed that perhaps during transmission a certain amount of audio-signal processing is performed by the various nerve interconnections such that further towards the brain, the nerve action potentials represent audio data that has been at least partially preprocessed before reaching the destinations in the audio cortex of the patient's brain), and different intensities of sensed audio at the various frequencies are used to calculate the repetition rates for the pulse data that are sent to different nerve pathways.

In some embodiments of the apparatus, the transmission medium includes a plurality of optical fibers each of which carries a different signal. In some such embodiments, the plurality of optical fibers each have one or more electrical conductors formed thereon, wherein each of a plurality of the electrical conductors carry a different signal.

In some embodiments of the apparatus, the transmission medium includes an optical fiber. In some embodiments of the apparatus, the transmission medium includes a lens. In some embodiments of the apparatus, the transmission medium delivers the light signals from the one or more light sources without using an optical fiber or a lens.

Some embodiments of the apparatus further includes a microphone having a signal output operatively coupled to a wireless transmitter that is configured to transmit information based on the microphone signal to the controller.

In some embodiments of the apparatus, the microphone further includes a processor that is configured to receive a sound signal and based on the sound signal to generate information used by the controller to generate stimulation pulses configured to be interpretable by the living animal's brain as having one or more frequency components and an intensity, in order to encode hearing.

In some embodiments of the apparatus, the one or more light sources further include one or more lasers. In some embodiments of the apparatus, the one or more light sources further include at least one tunable laser. In some embodiments of the apparatus, the one or more lasers output an infrared signal having a wavelength between about one micron and about five microns. In some embodiments of the apparatus, the one or more lasers output an infrared signal having a wavelength between about one micron and about two microns. In some embodiments of the apparatus, the one or more lasers output an infrared signal having a wavelength between about 1.8 microns and about 1.9 microns.

In some embodiments of the apparatus, the one or more lasers output an infrared signal having a wavelength between about 0.7 microns and about 0.8 microns. In some embodiments of the apparatus, the one or more lasers output an infrared signal having a wavelength between about 0.8 microns and about 0.9 microns. In some embodiments of the apparatus, the one or more lasers output an infrared signal having a wavelength between about 0.9 microns and about 1.0 microns. In some embodiments of the apparatus, the one or more lasers output an infrared signal having a wavelength between about 1.0 microns and about 1.1 microns. In some embodiments of the apparatus, the one or more lasers output an infrared signal having a wavelength between about 1.1 microns and about 1.2 microns. In some embodiments of the apparatus, the one or more lasers output an infrared signal having a wavelength between about 1.2 microns and about 1.3 microns. In some embodiments of the apparatus, the one or more lasers output an infrared signal having a wavelength between about 1.3 microns and about 1.4 microns. In some embodiments of the apparatus, the one or more lasers output an infrared signal having a wavelength between about 1.4 microns and about 1.5 microns. In some embodiments of the apparatus, the one or more lasers output an infrared signal having a wavelength between about 1.5 microns and about 1.6 microns. In some embodiments of the apparatus, the one or more lasers output an infrared signal having a wavelength between about 1.6 microns and about 1.7 microns. In some embodiments of the apparatus, the one or more lasers output an infrared signal having a wavelength between about 1.7 microns and about 1.8 microns. In some embodiments of the apparatus, the one or more lasers output an infrared signal having a wavelength between about 1.9 microns and about 2.0 microns. In some embodiments of the apparatus, the one or more lasers output an infrared signal having a wavelength between about 2.0 microns and about 2.1 microns. In some embodiments of the apparatus, the one or more lasers output an infrared signal having a wavelength between about 2.1 microns and about 2.3 microns. In some embodiments of the apparatus, the one or more lasers output an infrared signal having a wavelength between about 2.3 microns and about 2.5 microns. In some embodiments of the apparatus, the one or more lasers output an infrared signal having a wavelength between about 2.5 microns and about 5 microns. In some embodiments of the apparatus, the one or more lasers output an infrared signal having a wavelength between about 5 microns and about 10 microns.

In some embodiments of the apparatus, the one or more lasers output an infrared signal having a wavelength of about 1540 nanometers (1.54 microns). In some embodiments of the apparatus, the one or more lasers output an infrared signal having a wavelength of about 1800 nanometers. In some embodiments of the apparatus, the one or more lasers output an infrared signal having a wavelength of about 1849 nanometers. In some embodiments of the apparatus, the one or more lasers output an infrared signal having a wavelength of 1849 nanometers.

In some embodiments, the present invention further includes applying a precharge amount of stimulation electrical current to the neuronal tissue of the patient that is to be stimulated (e.g., to a plurality of nerve pathways the brainstem or midbrain of the patient), which is then followed by a trigger amount of pulsed light intensity of the plurality of light signals.

In some embodiments, the nerve stimulation includes an electrical current of about 0.1 mA to about 10 mA, plus an optical energy of about 0.01 J/cm$^2$ to about 1 J/cm$^2$. In some embodiments, the stimulation includes an electrical current of about 0.01 mA to about 0.02 mA between closely spaced electrodes (in some embodiments, the closely spaced electrodes include a metallization layer on each of two optical fibers that are both in one fiber-optic bundle; while in other embodiments, the closely spaced electrodes include separated portions of a metallization layer on a single optical fiber (e.g., wherein the metallization has been etched into a plurality of separate longitudinal conductors, and, in some embodiments, wherein the etching is helical around the optical fiber such that a twisted pair of conductors (or a plurality of such pairs) is formed, while in other embodiments, coaxial metallization layers are formed using an insulating layer to separate each pair of conduction layers). A current is sent through the separate conductors on the optical fiber and thus through the tissue that is adjacent to the light-emitting end of the optical-fiber waveguide such that the electrical field and the optical radiation are self aligned with one another. In some embodiments, the stimulation includes an electrical current of about 0.02 mA to about 0.05 mA between closely spaced electrodes. In some embodiments, the stimulation includes an electrical current of about 0.025 mA to about 0.035 mA between closely spaced electrodes. In some embodiments, the stimulation includes an electrical current of about 0.035 mA to about 0.05 mA between closely spaced electrodes. In some embodiments, the stimulation includes an electrical current of about 0.025 mA between closely spaced electrodes. In some embodiments, the stimulation includes an electrical current of about 0.035 mA between closely spaced electrodes. In some embodiments, the stimulation includes an electrical current of about 0.05 mA between closely spaced electrodes. In some embodiments, the stimulation includes an electrical current of about 0.1 mA between closely spaced electrodes. In some embodiments, the stimulation includes an electrical current of about 0.05 mA to about 0.1 mA between closely spaced electrodes. In some embodiments, the stimulation includes an electrical current of about 0.1 mA to about 0.2 mA between closely spaced electrodes. In some embodiments, the stimulation includes an electrical current of about 0.2 mA to about 0.5 mA between closely spaced electrodes. In some embodiments, the stimulation includes an electrical current of about 0.5 mA to about 1 mA between closely spaced electrodes. In some embodiments, the stimulation includes an electrical current of about 1 mA to about 2 mA between closely spaced electrodes. In some embodiments, the stimulation includes an electrical current of about 2 mA to about 5 mA between closely spaced electrodes. In some embodiments, the stimulation includes an electrical current of about 5 mA to about 10 mA between closely spaced electrodes.

In some embodiments, the pulse repetition rate of the optical signal is about 1 to 2 pulses per second. In some embodiments, the pulse repetition rate of the optical signal is about 2 to 5 pulses per second. In some embodiments, the pulse repetition rate of the optical signal is about 5 to 10 pulses per second. In some embodiments, the pulse repetition rate of the optical signal is about 10 to 20 pulses per second. In some embodiments, the pulse repetition rate of the optical signal is about 20 to 50 pulses per second. In some embodiments, the pulse repetition rate of the optical signal is about 50 to 100 pulses per second. In some embodiments, the pulse repetition rate of the optical signal is about 100 to 200 pulses per second. In some embodiments, the pulse repetition rate of the optical signal is about 200 to 500 pulses per second. In some embodiments, the pulse repetition rate of the optical signal is about 500 to 1000 pulses per second. In some embodiments, the pulse repetition rate of the optical signal is about 1000 to 2000 pulses per second. In some embodiments, the pulse repetition rate of the optical signal is more than about 2000 pulses per second.

In some embodiments of the apparatus, the one or more lasers output an infrared signal having a radiant exposure of no more than 4 $J/cm^2$ per nerve-action-potential response generated. In some embodiments of the apparatus, the one or more lasers output an infrared signal having a radiant exposure of no more than 3 $J/cm^2$ per nerve-action-potential response generated. In some embodiments of the apparatus, the one or more lasers output an infrared signal having a radiant exposure of no more than 2 $J/cm^2$ per nerve-action-potential response generated.

In some embodiments of the apparatus, the one or more lasers output an infrared signal having a radiant exposure of between about 5 $J/cm^2$ and about 6 $J/cm^2$ per nerve-action-potential response generated. In some embodiments of the apparatus, the one or more lasers output an infrared signal having a radiant exposure of between about 4 $J/cm^2$ and about 4 $J/cm^2$ per nerve-action-potential response generated. In some embodiments of the apparatus, the one or more lasers output an infrared signal having a radiant exposure of between about 3 $J/cm^2$ and about 4 $J/cm^2$ per nerve-action-potential response generated. In some embodiments of the apparatus, the one or more lasers output an infrared signal having a radiant exposure of between about 3 $J/cm^2$ and about 3.5 $J/cm^2$ per nerve-action-potential response generated. In some embodiments of the apparatus, the one or more lasers output an infrared signal having a radiant exposure of between about 2.5 $J/cm^2$ and about 3 $J/cm^2$ per nerve-action-potential response generated. In some embodiments of the apparatus, the one or more lasers output an infrared signal having a radiant exposure of between about 2 $J/cm^2$ and about 2.5 $J/cm^2$ per nerve-action-potential response generated. In some embodiments of the apparatus, the one or more lasers output an infrared signal having a radiant exposure of between about 1.5 $J/cm^2$ and about 2 $J/cm^2$ per nerve-action-potential response generated. In some embodiments of the apparatus, the one or more lasers output an infrared signal having a radiant exposure of between about 1 $J/cm^2$ and about 1.5 $J/cm^2$ per nerve-action-potential response generated. In some embodiments of the apparatus, the one or more lasers output an infrared signal having a radiant exposure of between about 0.5 $J/cm^2$ and about 1 $J/cm^2$ per nerve-action-potential response generated. In some embodiments of the apparatus, the one or more lasers output an infrared signal having a radiant exposure of between about 0.2 $J/cm^2$ and about 0.5 $J/cm^2$ per nerve-action-potential response generated. In some embodiments of the apparatus, the one or more lasers output an infrared signal having a radiant exposure of between about 0.1 $J/cm^2$ and about 0.2 $J/cm^2$ per nerve-action-potential response generated.

In some embodiments, the one or more lasers output an infrared signal having and energy of less than about 2 mJ per pulse.

In some embodiments, the one or more lasers output an infrared signal having a pulse width of between about ten microseconds (10 μs) and about five milliseconds (5 ms). In some embodiments, the one or more lasers output an infrared signal having a pulse width of between about 1 μs and about 10 μs. In some embodiments, the one or more lasers output an infrared signal having a pulse width of between about 10 μs and about 20 μs. In some embodiments, the one or more lasers output an infrared signal having a pulse width of between about 20 μs and about 50 μs. In some embodiments, the one or more lasers output an infrared signal having a pulse width of between about 20 μs and about 40 μs. In some embodiments, the one or more lasers output an infrared signal having a pulse width of between about 40 μs and about 80 μs. In some embodiments, the one or more lasers output an infrared signal having a pulse width of between about 80 μs and about 160 μs. In some embodiments, the one or more lasers output an infrared signal having a pulse width of between about 50 μs and about 100 μs. In some embodiments, the one or more lasers output an infrared signal having a pulse width of between about 100 μs and about 200 μs. In some embodiments, the one or more lasers output an infrared signal having a pulse width of between about 200 μs and about 500 μs. In some embodiments, the one or more lasers output an infrared signal having a pulse width of between about 200 μs and about 400 μs. In some embodiments, the one or more lasers output an infrared signal having a pulse width of between about 400 μs and about 800 μs. In some embodiments, the one or more lasers output an infrared signal having a pulse width of between about 800 μs and about 1600 μs. In some embodiments, the one or more lasers output an infrared signal having a pulse width of between about 500 μs and about 1000 μs. In some embodiments, the one or more lasers output an infrared signal having a pulse width of between about 1 millisecond (ms) and about 2 ms. In some embodiments, the one or more lasers output an infrared signal having a pulse width of between about 2 ms and about 5 ms. In some embodiments, the one or more lasers output an infrared signal having a pulse width of between about 2 ms and about 4 ms. In some embodiments, the one or more lasers output an infrared signal having a pulse width of between about 4 ms and about 8 ms. In some embodiments, the one or more lasers output an infrared signal having a pulse width of between about 8 ms and about 16 ms. In some embodiments, the one or more lasers output an infrared signal having a pulse width of between about 5 ms and about 10 ms.

In some embodiments, the present invention delivers a pulse of electrical current (as in existing devices called auditory brainstem implants) to the same site as light pulses. In some embodiments, the electrical pulses are below the threshold for neural excitation and the electric field spreads to a larger area than required for the region of interest (the area of specific nerve pathways to be stimulated). The light pulse from the apparatus of the present invention is delivered to match the exact volume of tissue that is to be stimulated: In some embodiments, the stimulation includes an electrical current of about 0.1 mA to about 10 mA, plus an optical energy of about 0.01 $J/cm^2$ to about 1 $J/cm^2$. Other parameters are determined by empirical experimentation, wherein the pulse repetition rate is generally about 10 to 1000 pulses per second.

In some such embodiments, the present invention provides a method that includes applying a combination of both an electrical stimulation signal and an optical stimulation signal to trigger a nerve action potential (NAP) in vivo in the brainstem or midbrain of an animal. In some embodiments of this method, the optical stimulation signal is of a nature such that if applied alone the optical signal has a low probability to trigger a NAP, the probability being no more than 25%. In some embodiments of this method, the electrical stimulation signal is of a nature such that if applied alone the electrical signal has a low probability to trigger a NAP, the probability being no more than 25%. In some embodiments of this method, the electrical stimulation signal is of a nature such that if applied alone the electrical signal has a low probability to trigger a NAP, the probability being no more than 25%. Some embodiments of this method further include also selectively applying a visible-indication light signal that indicates a location that the optical stimulation signal is to be applied.

Some embodiments of this method further include using a hybrid probe having an optical fiber inserted an electrically conductive cannula; applying the optical-stimulation signal through the optical fiber; and applying the electrical-stimulation signal through the cannula. Some embodiments further include delivering a fluid through the cannula to enhance the electrical interface for the electrical-stimulation signal and/or to enhance the optical interface for the optical-stimulation signal and/or to deliver one or more drugs to the stimulation site. Some embodiments further include withdrawing a fluid through the cannula to diagnose a condition. Some embodiments of this method further include using a second probe to obtain an electrical signal representative of the triggered NAP. Some embodiments of this method further include the hybrid probe further includes an electrode that is electrically separate from the cannula, and the method further includes using the electrode to obtain an electrical response signal representative of the triggered NAP. Some embodiments of this method further include using the cannula to obtain an electrical response signal representative of the triggered NAP.

In some embodiments of this method, a signal representative of the electrical stimulation signal is subtracted from a signal obtained using the cannula to obtain the electrical response signal representative of the triggered NAP.

Some embodiments of this method further include using a hybrid probe having an optical fiber that has a metallization layer applied to the optical fiber; applying the optical-stimulation signal through the optical fiber; and applying the electrical-stimulation signal through the metallization layer. Some embodiments of this method further include using a second probe to obtain an electrical response signal representative of the triggered NAP. In some embodiments of this method, the hybrid probe further includes an electrode that is electrically separate from the metallization layer, and the method further includes using the electrode to obtain an electrical response signal representative of the triggered NAP. Some embodiments of this method further include using the metallization layer to obtain an electrical response signal representative of the triggered NAP.

In some embodiments, the present invention provides an apparatus that includes an electrical-stimulation-signal source configured to selectively output an electrical stimulation signal; an optical-stimulation-signal source configured to selectively output an optical stimulation signal; and a controller and delivery medium operatively coupled to the electrical-stimulation-signal source and to the optical-stimulation-signal source and configured to control them and deliver the optical and electrical signals to trigger a nerve action potential (NAP) in vivo in the brainstem or midbrain of an animal.

In some embodiments of this apparatus, the optical stimulation signal is of a nature such that if applied alone the optical stimulation signal has a low probability to trigger a NAP, the probability being no more than 25%. In some embodiments of this apparatus, the electrical stimulation signal is of a nature such that if applied alone the electrical stimulation signal has a low probability to trigger a NAP, the probability being no more than 25%. In some embodiments of this apparatus, the electrical stimulation signal is of a nature such that if applied alone the electrical stimulation signal has a low probability to trigger a NAP, the probability being no more than 25%. In some embodiments of this apparatus, the optical stimulation signal is infrared, and the apparatus further includes a visible-indication-light-signal source configured to project visible light to indicate a location that the optical stimulation signal is to be applied. Some embodiments of this apparatus further include a hybrid probe having an optical fiber inserted an electrically conductive cannula, wherein the optical-stimulation signal is applied through the optical fiber and the electrical-stimulation signal is applied through the cannula. Some embodiments further include a second probe configured to obtain an electrical signal representative of the triggered NAP. In some embodiments, the hybrid probe further includes an electrode that is electrically separate from the cannula, wherein the electrode is configured to obtain an electrical signal representative of the triggered NAP. In some embodiments, the cannula is used to obtain an electrical signal representative of the triggered NAP. In some such embodiments, the apparatus is configured to subtract a signal representative of the electrical stimulation signal from a signal obtained using the cannula to obtain the electrical signal representative of the triggered NAP.

Some embodiments further include a hybrid probe having an optical fiber that has a metallization layer applied to the optical fiber, wherein the optical-stimulation signal is applied through the optical fiber and the electrical-stimulation signal is applied through the metallization layer. Some embodiments further include a second probe configured to obtain an electrical signal representative of the triggered NAP. In some embodiments, the hybrid probe further includes an electrode that is electrically separate from the metallization layer, and is configured to obtain an electrical signal representative of the triggered NAP. In some embodiments, the apparatus is configured to use the metallization layer to obtain an electrical signal representative of the triggered NAP.

In some embodiments, the present invention provides a method that includes obtaining a signal (such as an audio signal, a video signal, a gravitational orientation, an acceleration signal, a rotation signal, a temperature signal, a pressure signal or the like), and based on the sensed signal applying a combination of both an electrical stimulation signal and an optical stimulation signal to trigger a nerve action potential (NAP) in vivo in the cerebral cortex of an animal.

In some embodiments, the present invention provides an apparatus that includes an electrical-stimulation-signal source configured to selectively output an electrical stimulation signal; an optical-stimulation-signal source configured to selectively output an optical stimulation signal; and a controller and delivery medium operatively coupled to the electrical-stimulation-signal source and to the optical-stimulation-signal source and configured to control them and deliver the optical and electrical signals to trigger a nerve action potential (NAP) in vivo in the cerebral cortex of an animal.

In some embodiments, the present invention provides a method that includes receiving a signal, and based on the received signal applying a combination of both an electrical stimulation signal and an optical stimulation signal to trigger a nerve action potential (NAP) in vivo in the spinal cord of an animal.

In some embodiments, the present invention provides an apparatus that includes an electrical-stimulation-signal source configured to selectively output an electrical stimulation signal; an optical-stimulation-signal source configured to selectively output an optical stimulation signal; and a controller and delivery medium operatively coupled to the electrical-stimulation-signal source and to the optical-stimulation-signal source and configured to control them and deliver the optical and electrical signals to trigger a nerve action potential (NAP) in vivo in the spinal cord of an animal.

In some embodiments, the present invention delivers light pulses from vertical surface-emitting lasers (VCSELs). In some embodiments, electrical pulses are also delivered at below threshold for neural excitation and spread to larger area than required for the region of interest (the area to be stimulated). The light pulse is delivered to match the exact volume that is to be stimulated: In some embodiments, the electrical energy is about 0.1 mA to about 10 mA plus optical energy=0.01-1 J/cm$^2$; Other parameters are determined by empirical experimentation, wherein frequency is generally about 10 to 1000 pulses per second.

In some such embodiments, the present invention provides, in combination with others of the other embodiments described herein, one or more of the following: a method that includes emitting pulsed light having a wavelength in a range of 1.8 microns to 2 microns and having a pulse duration from each of a plurality of vertical cavity surface-emitting lasers (VC SELs) including a first VCSEL and a second VCSEL, directing the light from the first VCSEL onto a first tissue to stimulate the first tissue but substantially not onto a second tissue, and directing the light from the second VCSEL onto the second tissue to stimulate the second tissue but substantially not onto the first tissue; such a method but further including emitting pulsed light having a wavelength in a range of 650 nm to 850 nm and having a pulse duration from each of a plurality of vertical cavity surface-emitting lasers (VCSELs) including a third VCSEL and a fourth VCSEL, directing the light from the third VCSEL onto the first tissue and illuminating the first tissue but substantially not illuminating the second tissue, detecting a reflected light from the first tissue and determining a first physiological activity of the first tissue, directing the light from the fourth VCSEL onto the second tissue and illuminating the second tissue but substantially not illuminating the first tissue, and detecting a reflected light from the second tissue and determining a second physiological activity of the second tissue. In some such embodiments, the first VCSEL and the second VCSEL are located on a single semiconductor substrate. In some such embodiments, the third VCSEL and the fourth VCSEL are located on a single semiconductor substrate. In some such embodiments, the first VCSEL, the second VCSEL, the third VCSEL and the fourth VCSEL are located on a single semiconductor substrate. Some embodiments further include integrating a first microlens with the first VCSEL and focusing the pulsed light from the first VCSEL onto the first tissue, integrating a second microlens with the second VCSEL and focusing the pulsed light from the second VCSEL onto the second tissue, integrating a third microlens with the third VCSEL and focusing the pulsed light from the third VCSEL onto the first tissue, and integrating a fourth microlens with the fourth VCSEL and focusing the pulsed light from the fourth VCSEL onto the second tissue. Some embodiments further include providing a fiber optic bundle including a plurality of optical fibers, integrating a first optical fiber with the first VCSEL and directing the pulsed light from the first VCSEL onto the first tissue, integrating a second optical fiber with the second VCSEL and directing the pulsed light from the second VCSEL onto the second tissue, integrating a third optical fiber with the third VCSEL and directing the pulsed light from the third VCSEL onto the first tissue, and integrating a fourth optical fiber with the fourth VCSEL and directing the pulsed light from the fourth VCSEL onto the second tissue. In some embodiments, each optical fiber in the plurality of optical fibers includes a lens. In some embodiments, the first VCSEL and the third VCSEL are integrated into a first flex-cuff ring and the second VCSEL and the third VCSEL are integrated into a second flex-cuff ring. In some embodiments, the first VCSEL, the second VCSEL, the third VCSEL and the fourth VCSEL are mounted in a biocompatible housing having an optical feed through.

In some such embodiments, the present invention provides an apparatus that includes a plurality of vertical cavity surface-emitting lasers (VCSELs) including a first VCSEL and a second VCSEL; a control circuit configured to control generation of pulsed light from the first and second VCSELs; and a light-delivery system configured to direct the light from the first VCSEL onto a first tissue but substantially not onto a second tissue in order to stimulate the first tissue; wherein the light-delivery system is further configured to direct the light from the second VCSEL onto the second tissue but substantially not onto the first tissue in order to stimulate the second tissue. In some embodiments, the apparatus further includes a plurality of vertical cavity surface-emitting lasers (VCSELs) including a third VCSEL and a fourth VCSEL. The control circuit is further configured to control generation of pulsed light from the third and fourth VCSELs; the light delivery system is further configured to direct the light from the third VCSEL onto a first tissue but substantially not onto a second tissue in order to illuminate the first tissue; the light delivery system is further configured to direct the light from the fourth VCSEL onto the second tissue but substantially not onto the first tissue in order to illuminate the second tissue; a plurality of detectors including a first detector and a second detector; the first detector is configured to detect reflected light from the first tissue to determine a first physiological activity in the first tissue; and the second detector is configured to detect reflected light from the second tissue to determine a second physiological activity in the second tissue. In some embodiments, the first VCSEL and the second VCSEL are provided on a single semiconductor substrate. In some embodiments, the third VCSEL and the fourth VCSEL are provided on a single semiconductor substrate. In some embodiments, the first VCSEL, the second VCSEL, the third VCSEL and the fourth VCSEL are provided on a single semiconductor substrate. Some embodiments further include a first microlens integrated with the first VCSEL to focus the pulsed light from the first VCSEL onto the first tissue; a second microlens integrated with the second VCSEL to focus the pulsed light from the second VCSEL onto the second tissue; a third microlens integrated with the third VCSEL to focus the pulsed light from the third VCSEL onto the first tissue; and a fourth microlens integrated with the fourth VCSEL to focus the pulsed light from the fourth VCSEL onto the second tissue. Some embodiments further include a fiber optic bundle including a plurality of optical fibers, each optical fiber having a first end and a second end; a first optical fiber operatively coupled at the first end of the first optical fiber to the first VCSEL to direct the pulsed light from the first VCSEL through the first optical fiber and the second end of the first optical fiber onto the first tissue; a second optical fiber operatively coupled at the first end of the second optical fiber to the second VCSEL to direct the pulsed light from the second VCSEL through the second optical fiber and the second end of the second optical fiber onto the second tissue; a third optical fiber operatively coupled at the first end of the third optical fiber to the third VCSEL to direct the pulsed light from the third VCSEL through the third optical fiber and the second end of the third optical fiber onto the first tissue; and a fourth optical fiber operatively coupled at the first end of the fourth optical fiber to the fourth VCSEL to direct the pulsed light from the fourth VCSEL through the fourth optical fiber and the second end of the fourth optical fiber onto the second tissue. In some embodiments, each optical fiber in the plurality of optical fibers includes a lens. In some embodiments, the first VCSEL and the third VCSEL are integrated into a first flex-cuff ring and the second VCSEL and the third VCSEL are integrated into a second flex-cuff ring. In some embodiments, the first VCSEL, the second VCSEL, the third VCSEL and the fourth VCSEL are mounted in a biocompatible housing having an optical feed through.

The present invention also contemplates various combinations and subcombinations of the embodiments set forth in the above description.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A method for stimulating neurons of a brainstem or midbrain of a patient to provide sensations for the patient, the method comprising:

generating a plurality of light signals that, when applied to a neuron of a person, directly stimulates a nerve action potential in the neuron;

delivering the light signals to a plurality of neurons of the brainstem or midbrain of the patient;

selectively controlling the plurality of light signals to directly optically stimulate the plurality of neurons in order to control nerve action potentials (NAPs) produced by the plurality of neurons;

receiving sensed electromagnetic-radiation data indicative of a color; and processing the received electromagnetic-radiation data to obtain color information, wherein the delivering of light signals comprises delivering the light pulses to a vision portion of the brainstem or midbrain of the patient to provide a sensation of the color to the patient.

2. The method of claim 1, the method further comprising: receiving image data; and processing the received image data to detect object-pattern information including vertical-object, horizontal-object, diagonal-object, and curved-object pattern information, wherein the delivering of light signals further comprises delivering the light pulses to a vision portion of the brainstem or midbrain of the patient to provide a sensation of the pattern to the patient.

3. A method for stimulating neurons of a brainstem or midbrain of a patient to provide sensations for the patient, the method comprising:

generating a plurality of light signals that, when applied to a neuron of a person, can stimulate a nerve action potential in the neuron;

delivering the light signals to a plurality of neurons of the brainstem or midbrain of the patient;

selectively controlling the plurality of light signals to directly optically stimulate the plurality of neurons in order to control nerve action potentials (NAPs) produced by the plurality of neurons;

receiving an audio signal; and processing the received audio signal to obtain frequency and intensity information, wherein the delivering of light signals comprises delivering the light pulses to an auditory portion of the brainstem or midbrain of the patient, and wherein the selectively controlling of the light signals includes selectively controlling the light signals to emit light pulses to selected locations of the brainstem or midbrain of the patient based on the frequency information and at selected pulse-repetition rates based on the intensity information.

4. The method of claim 2, further comprising delivering an electrical signal to the plurality of neurons of the auditory portion of the brainstem or midbrain of the patient, such that a combination of the electrical signal and the light signals stimulate the nerve action potentials in the plurality of neurons.

5. The method of claim 3, wherein the delivering of light signals further includes delivering infrared light from a laser.

6. The method of claim 3, wherein the delivering of light signals further includes delivering infrared light from a vertical-cavity surface-emitting laser (VCSEL).

7. The method of claim 3, wherein the delivering of light signals further includes delivering the light signals to peripheral projections of the neurons.

8. The method of claim 3, wherein the delivering of light signals further includes delivering the light signals to central portions of the neurons.

9. The method of claim 3, wherein the delivering of the light signals further includes obtaining a plurality of light signals from one or more laser light sources and delivering the obtained light signals to discrete portions of excitable tissues, said signals being interpretable by the patient's brain as sensory responses.

10. The method of claim 3, wherein the delivering of the light signals further includes selectively controlling the light signals to optically stimulate the plurality of neurons in order to control nerve action potentials (NAPs) produced by the plurality of neurons.

11. An apparatus comprising:
one or more light sources that are configured to generate a plurality of pulsed light signals that, when applied to a neuron of a person, directly stimulates a nerve action potential in the neuron;
a transmission medium configured to transmit the plurality of light signals from the one or more light sources to a plurality of neurons of a brainstem or midbrain of a living animal to provide auditory sensations for the living animal; and
a controller operatively coupled to the one or more light sources to selectively control the plurality of pulsed light signals from each of the one or more light sources such that the light signals provide controlled optical stimulation directly to the plurality of neurons in order to control nerve action potentials (NAPs) produced by the plurality of neurons, wherein the controller processes a received audio signal to obtain frequency and intensity information, and uses the transmission medium to deliver the pulsed light signals to selected locations of the brainstem or midbrain of the patient based on the frequency information, and wherein the controller controls the pulsed light signals at selected pulse-repetition rates based on the intensity information.

12. The apparatus of claim 11, wherein the control of the light signals provided by the controller includes selective control of a duty cycle of the plurality of light signals.

13. The apparatus of claim 11, wherein the control of the light signals provided by the controller includes selective control of a wavelength of the plurality of light signals.

14. The apparatus of claim 11, wherein the transmission medium includes a plurality of optical-signal-transmission channels.

15. The apparatus of claim 14, wherein the transmission medium includes a plurality of optical fibers each of which carries a different signal.

16. The apparatus of claim 11, further comprising a microphone having a signal output operatively coupled to a wireless transmitter that is configured to transmit information based on the microphone signal to the controller.

17. The apparatus of claim 16, the microphone further comprising a processor that is configured to receive a sound signal and based on the sound signal to generate information used by the controller to generate stimulation pulses configured to be interpretable by the living animal's brain as having one or more frequency components and an intensity, in order to encode hearing.

18. The apparatus of claim 11, wherein the one or more light sources includes a plurality of vertical-cavity surface-emitting lasers (VCSELs).

19. The apparatus of claim 11, wherein the transmission medium includes an optical fiber.

20. An apparatus for stimulating neurons of a brainstem or midbrain of a patient to provide sensations for the patient, the apparatus comprising:
means for generating a plurality of light signals that, when applied to a neuron of a person, directly stimulates a nerve action potential in the neuron;
means for delivering the light signals to a plurality of neurons of the brainstem or midbrain of the patient; and
means for selectively controlling the plurality of light signals to directly optically stimulate the plurality of neurons in order to control nerve action potentials (NAPs) produced by the plurality of neurons;
means for receiving sensed electromagnetic-radiation data indicative of a color; and
means for processing the received electromagnetic-radiation data to obtain color information, wherein the means for delivering of light signals comprises means for delivering the light pulses to a vision portion of the brainstem or midbrain of the patient to provide a sensation of the color to the patient.

21. An apparatus for stimulating neurons of a brainstem or midbrain of a patient to provide sensations for the patient, the apparatus comprising:
means for generating a plurality of light signals that, when applied to a neuron of a person, directly stimulates a nerve action potential in the neuron;
means for delivering the light signals to a plurality of neurons of the brainstem or midbrain of the patient;
means for selectively controlling the plurality of light signals to directly optically stimulate the plurality of neurons in order to control nerve action potentials (NAPs) produced by the plurality of neurons;
means for receiving an audio signal; and
means for processing the received audio signal to obtain frequency and intensity information, wherein the delivering of light signals comprises delivering the light pulses to an auditory portion of the brainstem or midbrain of the patient, and wherein the means for selectively controlling of the light signals includes means for selectively controlling the light signals to emit light pulses to selected locations of the brainstem or midbrain of the patient based on the frequency information and at selected pulse-repetition rates based on the intensity information.

22. The apparatus of claim 21, further comprising means for delivering an electrical signal to the plurality of neurons of the auditory portion of the brainstem or midbrain of the patient, such that a combination of the electrical signal and the light signals stimulate the nerve action potentials in the plurality of neurons.

* * * * *

UNITED STATES PATENT AND TRADEMARK OFFICE
CERTIFICATE OF CORRECTION

| | | |
|---|---|---|
| PATENT NO. | : 8,744,570 B2 | Page 1 of 1 |
| APPLICATION NO. | : 12/693427 | |
| DATED | : June 3, 2014 | |
| INVENTOR(S) | : Daniel J. Lee and Jonathon D. Wells | |

It is certified that error appears in the above-identified patent and that said Letters Patent is hereby corrected as shown below:

Title page, item [73] Assignees: should read as follows:
Lockheed Martin Corporation, Bethesda, MD (US);
Massachusetts Eye and Ear Infirmary, Boston, MA (US)

Signed and Sealed this
Thirtieth Day of December, 2014

Michelle K. Lee
*Deputy Director of the United States Patent and Trademark Office*